(12) United States Patent
Schraga

(10) Patent No.: US 9,770,200 B2
(45) Date of Patent: Sep. 26, 2017

(54) NEEDLE ASSEMBLY WITH SAFETY SYSTEM FOR A SYRINGE OR FLUID SAMPLING DEVICE AND METHOD OF MAKING AND USING THE SAME

(71) Applicant: STAT MEDICAL DEVICES, INC., N. Miami Beach, FL (US)

(72) Inventor: Steven Schraga, Surfside, FL (US)

(73) Assignee: STAT MEDICAL DEVICES, INC., N. Miami Beach ( * ) Notice: Subject to any disclaimer, the term of this patent is extended or adjusted under 35 U.S.C. 154(b) by 0 days.

(21) Appl. No.: 14/737,117

(22) Filed: Jun. 11, 2015

(65) Prior Publication Data
US 2015/0272492 A1    Oct. 1, 2015

Related U.S. Application Data

(63) Continuation of application No. 13/719,933, filed on Dec. 19, 2012, now Pat. No. 9,078,978.
(Continued)

(51) Int. Cl.
*A61M 5/00*    (2006.01)
*A61B 5/15*    (2006.01)
(Continued)

(52) U.S. Cl.
CPC ........ *A61B 5/150648* (2013.01); *A61B 5/153* (2013.01); *A61B 5/15003* (2013.01); *A61B 5/150183* (2013.01); *A61B 5/150389* (2013.01); *A61B 5/150503* (2013.01); *A61B 5/150572* (2013.01); *A61B 5/150603* (2013.01); *A61B 5/150702* (2013.01); *A61B 5/150732* (2013.01); *A61B 5/150893* (2013.01);
(Continued)

(58) Field of Classification Search
CPC ............ A61B 5/150572; A61B 5/1405; A61B 5/15003; A61B 5/150183; A61B 5/150389; A61B 5/150503; A61B 5/150603; A61B 5/150648; A61B 5/150702; A61B 5/150732; A61B 5/150893; A61B 5/150916; A61B 5/153; A61M 5/3213; A61M 5/46; A61M 5/5086; A61J 1/2096; A61J 2001/201
USPC ....................................................... 604/110
See application file for complete search history.

(56) References Cited

U.S. PATENT DOCUMENTS 4,490,142 A    12/1984   Silvern
4,813,426 A    3/1989    Haber et al.
(Continued)

FOREIGN PATENT DOCUMENTS

EP    2 251 054    11/2010
WO    99/08742     2/1999
(Continued)

*Primary Examiner* — Jason Flick
(74) *Attorney, Agent, or Firm* — Thomas|Horstemeyer LLP; Randy R. Schoen

(57) ABSTRACT

Needle assembly having the following modes of operation; a first mode wherein the safety shield can move to a first retracted position allowing injection of the piercing portion of needle from a position at least partially covering the piercing portion of the needle and a second mode wherein the safety shield moves to a position protecting the piercing portion of the needle after the first mode and is prevented from moving back to a position exposing the piercing portion of the needle.

16 Claims, 34 Drawing Sheets

Related U.S. Application Data

(60) Provisional application No. 61/580,951, filed on Dec. 28, 2011.

(51) Int. Cl.
  *A61M 5/32* (2006.01)
  *A61M 5/50* (2006.01)
  *A61M 5/46* (2006.01)
  *A61B 5/153* (2006.01)
  *A61J 1/20* (2006.01)

(52) U.S. Cl.
  CPC ..... *A61B 5/150916* (2013.01); *A61M 5/3202* (2013.01); *A61M 5/3213* (2013.01); *A61M 5/3257* (2013.01); *A61M 5/3293* (2013.01); *A61M 5/46* (2013.01); *A61M 5/5086* (2013.01); *A61J 1/201* (2015.05); *A61J 1/2096* (2013.01)

(56) References Cited

U.S. PATENT DOCUMENTS

| | | |
|---|---|---|
| 4,822,343 A | 4/1989 | Beiser |
| 4,838,863 A | 6/1989 | Allard et al. |
| 4,894,055 A | 1/1990 | Sudnak |
| 4,904,244 A | 2/1990 | Harsh et al. |
| 4,907,600 A | 3/1990 | Spencer |
| 4,909,792 A | 3/1990 | Norelli |
| 4,915,702 A | 4/1990 | Haber |
| 4,973,318 A | 11/1990 | Holm et al. |
| 4,984,580 A | 1/1991 | Wanamaker |
| 4,993,426 A | 2/1991 | Spencer |
| 4,994,034 A | 2/1991 | Botich et al. |
| 5,049,133 A | 9/1991 | Villen Pascual |
| 5,114,410 A | 5/1992 | Caralt Batlle |
| 5,117,837 A | 6/1992 | Wanamaker et al. |
| 5,125,898 A | 6/1992 | Kaufhold, Jr. |
| 5,180,370 A | 1/1993 | Gillespie |
| 5,242,401 A | 9/1993 | Colsky |
| 5,242,416 A | 9/1993 | Hutson |
| 5,376,080 A | 12/1994 | Petrussa |
| 5,385,551 A | 1/1995 | Shaw |
| 5,389,085 A | 2/1995 | D'Alessio et al. |
| 5,407,436 A | 4/1995 | Toft et al. |
| 5,419,773 A | 5/1995 | Rupp |
| 5,423,758 A | 6/1995 | Shaw |
| 5,454,828 A | 10/1995 | Schraga |
| 5,578,011 A | 11/1996 | Shaw |
| 5,591,138 A * | 1/1997 | Vaillancourt ....... A61M 5/3271 604/192 |
| 5,593,387 A | 1/1997 | Rupp |
| 5,611,786 A | 3/1997 | Kirchhofer et al. |
| 5,616,136 A | 4/1997 | Shillington et al. |
| 5,632,733 A | 5/1997 | Shaw |
| 5,637,101 A | 6/1997 | Shillington et al. |
| 5,755,673 A | 5/1998 | Kinsey |
| 5,797,490 A | 8/1998 | Fujii et al. |
| 5,810,775 A | 9/1998 | Shaw |
| 5,980,488 A | 11/1999 | Thorne |
| 6,015,438 A | 1/2000 | Shaw |
| 6,024,710 A | 2/2000 | Miller |
| 6,083,199 A | 7/2000 | Thorley et al. |
| 6,117,108 A | 9/2000 | Woehr et al. |
| 6,171,284 B1 | 1/2001 | Kao et al. |
| D445,602 S | 7/2001 | Tonon |
| 6,287,278 B1 | 9/2001 | Woehr et al. |
| 6,379,333 B1 | 4/2002 | Brimhall et al. |
| 6,391,003 B1 | 5/2002 | Lesch, Jr. |
| 6,432,087 B1 | 8/2002 | Hoeck et al. |
| 6,460,234 B1 | 10/2002 | Gianchandani |
| 6,470,754 B1 | 10/2002 | Gianchandani |
| 6,517,516 B1 | 2/2003 | Caizza |
| 6,572,565 B2 | 6/2003 | Daley et al. |
| 6,616,630 B1 | 9/2003 | Woehr et al. |
| 6,652,490 B2 | 11/2003 | Howell |
| 6,749,588 B1 | 6/2004 | Howell et al. |
| 6,855,129 B2 | 2/2005 | Jensen et al. |
| 6,932,793 B1 | 8/2005 | Marshall et al. |
| RE38,964 E | 1/2006 | Shillington |
| RE39,107 E | 5/2006 | Shaw |
| 7,125,397 B2 | 10/2006 | Woehr et al. |
| 7,214,211 B2 | 5/2007 | Woehr et al. |
| 7,264,613 B2 | 9/2007 | Woehr et al. |
| 7,462,168 B2 | 12/2008 | Stonehouse et al. |
| 7,500,967 B2 | 3/2009 | Thorley et al. |
| 7,521,022 B2 | 4/2009 | Konrad |
| 7,540,858 B2 | 6/2009 | DiBiasi |
| 7,553,293 B2 | 6/2009 | Jensen et al. |
| 7,871,397 B2 | 1/2011 | Schraga |
| 7,935,087 B2 | 5/2011 | Judd et al. |
| 8,002,745 B2 | 8/2011 | Kaal et al. |
| 8,012,132 B2 | 9/2011 | Lum et al. |
| 8,021,333 B2 | 9/2011 | Kaal et al. |
| 8,052,654 B2 | 11/2011 | Kaal et al. |
| 8,114,050 B2 | 2/2012 | Kaal et al. |
| 8,147,450 B2 | 4/2012 | Yang |
| 9,078,978 B2 | 7/2015 | Schraga |
| 2002/0004648 A1 | 1/2002 | Larsen et al. |
| 2002/0133122 A1 | 9/2002 | Giambattista et al. |
| 2003/0014018 A1 | 1/2003 | Giambattista et al. |
| 2003/0105431 A1 | 6/2003 | Howell |
| 2003/0195471 A1 | 10/2003 | Woehr et al. |
| 2004/0116856 A1 | 6/2004 | Woehr et al. |
| 2004/0186434 A1 | 9/2004 | Harding et al. |
| 2004/0204681 A1 | 10/2004 | Thoresen et al. |
| 2004/0236284 A1 | 11/2004 | Hoste et al. |
| 2004/0236288 A1 | 11/2004 | Howell |
| 2005/0004532 A1 | 1/2005 | Woehr et al. |
| 2005/0038392 A1 | 2/2005 | DeSalvo |
| 2005/0080378 A1 | 4/2005 | Cindrich et al. |
| 2005/0107748 A1 | 5/2005 | Thorne et al. |
| 2005/0159705 A1 | 7/2005 | Crawford et al. |
| 2005/0277881 A1 | 12/2005 | Sibbitt |
| 2005/0277895 A1 | 12/2005 | Giambattista et al. |
| 2005/0283115 A1 | 12/2005 | Giambattista et al. |
| 2006/0229652 A1 | 10/2006 | Iio et al. |
| 2006/0264828 A1 | 11/2006 | Woehr et al. |
| 2007/0049868 A1 | 3/2007 | Woehr et al. |
| 2007/0083159 A1 | 4/2007 | Woehr et al. |
| 2007/0100297 A1 | 5/2007 | Woehr et al. |
| 2007/0129689 A1 | 6/2007 | Woehr et al. |
| 2007/0203458 A1 | 8/2007 | Tsubota |
| 2008/0108951 A1 | 5/2008 | Jerde et al. |
| 2008/0154192 A1 | 6/2008 | Schraga |
| 2008/0177237 A1 | 7/2008 | Stonehouse et al. |
| 2008/0177238 A1 | 7/2008 | Follman et al. |
| 2008/0262421 A1 | 10/2008 | Schraga |
| 2009/0069753 A1 | 3/2009 | Ruan et al. |
| 2009/0254042 A1 | 10/2009 | Gratwohl |
| 2010/0262119 A1 | 10/2010 | Schraga |
| 2010/0286558 A1 | 11/2010 | Schraga |
| 2010/0292654 A1 | 11/2010 | Schraga |
| 2011/0022001 A1 | 1/2011 | Wei |
| 2011/0077615 A1 | 3/2011 | Schraga |
| 2011/0106016 A1 | 5/2011 | Wei |
| 2011/0118667 A1 | 5/2011 | Zaiken et al. |
| 2011/0125130 A1 | 5/2011 | Schraga |
| 2011/0160613 A1 | 6/2011 | Schraga |
| 2011/0160675 A1 | 6/2011 | Ruan et al. |
| 2011/0213304 A1 | 9/2011 | Schraga |

FOREIGN PATENT DOCUMENTS

| | | |
|---|---|---|
| WO | 00/69501 | 11/2000 |
| WO | WO 2008/077706 | 7/2008 |

* cited by examiner

NEEDLE ASSEMBLY WITH SAFETY SYSTEM FOR A SYRINGE OR FLUID SAMPLING DEVICE AND METHOD OF MAKING AND USING THE SAME

CROSS-REFERENCE TO RELATED APPLICATIONS

The instant application is a continuation of U.S. nonprovisional application Ser. No. 13/719,933 filed on Dec. 19, 2012, which is based on and claims the benefit of U.S. provisional application No. 61/580,951, filed Dec. 28, 2011, the disclosure of each of these applications is hereby expressly incorporated by reference thereto in their entireties.

BACKGROUND OF THE INVENTION

1. Field of the Invention

This invention relates generally to devices used to inject or withdraw fluid and/or those that collect fluid samples from and/or inject fluids into patients and/or into a fluid collection, dispensing or holding device. More specifically, this invention relates to a needle assembly for such devices which have a safety system.

2. Discussion of Background Information

Prevention of needle sticks is of paramount concern in the healthcare industry because of serious and deadly risk factors associated with AIDS and other serious transmittable or communicable diseases. Typical injection and/or blood collection devices utilize a needle which can be, among other things, inserted into a patient so as to inject a substance or draw a fluid such as blood through the needle into an associated separate collection reservoir. Accidental needle sticks from currently or previously used needles can occur during the process of injection and during the fluid withdrawing process as well as during subsequent handling and disposal. Until such used medical devices are destroyed or discarded into a proper disposal collection device such as a sharps container, they remain a risk to those handling them as well as those that may come into contact with them.

Devices used for injection as well as blood sampling are well known and include a collection device sold under the trademark Vacutainer® by Becton Dickinson Corporation. The former type device includes syringes. The latter type device has a tubular syringe-like body with a needle in the front end, part of which extends back into a tubular syringe-like shell. Part of the needle extends externally for punching the skin. An evacuated collection tube with a rubber stopper is placed into the open back of the syringe-like shell with the rubber stopper against the internal end of the needle. After the skin is punctured, the collection tube is pushed forward to cause the needle to enter the evacuated tube. Vacuum helps draw blood into the collecting tube. When a sufficient sample has been obtained, the collecting tube and the stopper are simply withdrawn from the tubular shell and sent to the laboratory. This particular device has a permanently extended needle and an opening in the back for the collection tube which remains open after the collection tube is removed, leaving small droplets of blood or fluids and/or small quantities of blood or fluids and an internally exposed needle.

Medical injection devices which are used for drawing and/or injecting fluids and which may or may not include a common or standard interface are known. Such devices include: U.S. Pat. No. 6,074,373 to SUDO et al. and U.S. Pat. No. 8,012,132 to LUM et al. The disclosures of each of these documents is expressly incorporated by reference herein in their entireties.

Medical devices which are used for collecting fluid samples from patients which have quick release needle systems are also known. Such devices include: U.S. Pat. No. 5,797,490 to FUJI et al; U.S. Pat. No. 5,755,673 to KINSEY; U.S. Pat. No. 4,822,343 to BEISER; U.S. Pat. No. 4,984,580 WANAMAKER; U.S. Re. 38,964 to SHILLINGTON; U.S. Pat. No. 5,616,136 to SHILLINGTON et al.; U.S. Pat. No. 5,637,101 to SHILLINGTON; U.S. Pat. No. 5,117,837 to WANAMAKER et al.; U.S. Pat. No. 4,907,600 to SPENCER; U.S. Pat. No. 4,993,426 to SPENCER; U.S. Pat. No. 4,904,244 to HARSH et al.; U.S. Pat. No. 4,490,142 to SILVERN. The disclosures of each of these documents is expressly incorporated by reference herein in their entireties.

Medical devices which are used for collecting fluid samples from patients which can benefit from the improvement offered by the instant invention include: US 2010/0286558 to SCHRAGA; US 2008/0262421 to SCHRAGA; U.S. Ser. No. 12/974,908 to SCHRAGA filed on Dec. 21, 2010; and U.S. 61/480,787 to SCHRAGA filed on Apr. 29, 2011. The disclosures of each of these documents is expressly incorporated by reference herein in their entireties.

Pen needle or pre-loaded syringe devices which utilize needle safety shields are also known. These include: US 2011/0160675 to RUAN et al.; US 2011/0257603 to RUAN et al.; US 2011/0288491 to NEWMAN et al. The disclosures of each of these documents is expressly incorporated by reference herein in their entireties.

Devices having one or more features which can be used with the invention and which are disclosed in pending applications include: US 2010/0286611 to SCHRAGA; US 2010/0286558 to SCHRAGA; U.S. 61/443,958 to SCHRAGA; U.S. 61/480,787 to SCHRAGA; U.S. 61/498,133 to SCHRAGA. The disclosures of each of these documents are expressly incorporated by reference herein in their entireties.

The invention aims to improve devices of the type described above by making a needle assembly for an injection or fluid collection device which a needle safety system and/or a standard interface needle and which can also include one or more features disclosed herein and/or disclosed in one or more of the documents expressly incorporated by reference herein. The device is also believed to be as safe or safer to use and/or dispose-of than the above-noted devices.

SUMMARY OF THE INVENTION

In accordance with one non-limiting aspect of the invention, there is provided a needle assembly, comprising a body having a front portion, a back portion, and a wall or needle support separating the front and back portions. A needle has a piercing portion projecting forwardly from the wall or needle support. A safety shield is axially movable relative to the body at least between an initial position, a retracted position, and a post use locking position.

In embodiments, the safety shield is at least partially disposed within the front portion of the body, includes a locking system which is prevented from being contacted by a user's fingers, and moves linearly without also rotating.

In embodiments, the safety shield, alternatively and/or additionally, rotates at least partially in opposite directions as it moves from the initial position to the retracted position.

In embodiments, the safety shield, alternatively and/or additionally, rotates at least partially in opposite directions as it moves from the initial position to the retracted position.

In embodiments, the safety shield, alternatively and/or additionally, includes at least one projection that extends into a guide recess comprising at least a linear section and a curved section.

In embodiments, the safety shield, alternatively and/or additionally, includes at least one projection that extends into a guide recess comprising at least a linear section and an angled section.

In embodiments, the safety shield, alternatively and/or additionally, includes at least one projection that extends into a guide recess comprising at least one locking mechanism for retaining the safety shield in the post use locking position.

In embodiments, the safety shield, alternatively and/or additionally, includes at least one mechanism for preventing a locking of the safety shield when said shield in not in the post use locking position.

In embodiments, the safety shield, alternatively and/or additionally, includes at least one mechanism for providing a visual indication to the user that the needle tip has been used, wherein the visual indication is arranged on a skin engaging end of the safety shield.

In embodiments, the safety shield, alternatively and/or additionally, includes a first portion that is at least partially disposed within the front portion of the body, a second portion that at least partially covers the front portion, and has its movement limited by engagement between at least one projection extending into a guide recess.

In embodiments, the injection device is a syringe having a standard interface.

In embodiments, the standard interface is a luer-lok interface.

In embodiments, the injection device is a fluid collection device.

In embodiments, the fluid collection device has a standard or common interface.

In embodiments, the standard interface is a Luer-lok interface.

In embodiments, the needle assembly has the following modes of operation when installed on the injection device; a first mode wherein the safety shield can move to a first retracted position during injection of the piercing portion of needle into a container containing a substance that can be suctioned into the injection device, a second mode wherein the safety shield automatically moves to a position protecting the piercing portion of the needle after the first mode, a third mode wherein the safety shield can move to a second retracted position during injection of the piercing portion of needle into a surface which will receive the substance forced out of the injection device, and a fourth mode wherein the safety shield automatically moves to a position protecting the piercing portion of the needle after the third mode.

In embodiments, the needle assembly has the following modes of operation when installed on the injection device; a first mode wherein the safety shield can move to a first retracted position during injection of the piercing portion of needle into a container containing a substance that can be suctioned into the injection device, a second mode wherein the safety shield automatically moves to a position protecting the piercing portion of the needle after the first mode, a third mode wherein the safety shield can move to a second retracted position during injection of the piercing portion of needle into a surface which will receive the substance forced out of the injection device, and a fourth mode wherein the safety shield automatically moves to a position protecting the piercing portion of the needle after the third mode and is locked in this position so as to prevent re-use or re-injection of the needle.

In embodiments, the needle assembly has the following modes of operation when installed on the injection device; a first mode wherein the safety shield can move to a first retracted position during injection of the piercing portion of needle into a container containing a substance that can be suctioned into the injection device, a second mode wherein the safety shield automatically moves to a position protecting the piercing portion of the needle after the first mode, a third mode wherein the safety shield can move to a second retracted position during injection of the piercing portion of needle into a surface which will receive the substance forced out of the injection device, and a fourth mode wherein the safety shield automatically moves to a position protecting the piercing portion of the needle after the third mode and is automatically locked in this position so as to prevent re-use or re-injection of the needle.

In embodiments, the needle assembly has the following modes of operation when installed on the injection device; a first mode wherein the safety shield can move to a first retracted position during injection of the piercing portion of needle into a container containing a substance that can be suctioned into the injection device, a second mode wherein the safety shield automatically moves to a position protecting the piercing portion of the needle after the first mode, a third mode wherein the safety shield can move to a second retracted position during injection of the piercing portion of needle into a surface which will receive the substance forced out of the injection device, and a fourth mode wherein the safety shield moves to a position protecting the piercing portion of the needle after the third mode and is prevented from moving back to a position exposing the piercing portion of the needle.

In embodiments, the needle assembly has the following modes of operation when installed on the injection device having the form of a syringe; a first mode wherein the safety shield can move to a first retracted position during injection of the piercing portion of needle into a medicine container containing a medicine that can be suctioned into the syringe, a second mode wherein the safety shield automatically moves to a position protecting the piercing portion of the needle after the first mode, a third mode wherein the safety shield can move to a second retracted position during injection of the piercing portion of needle into a skin surface which will receive the medicine forced out of the syringe, and a fourth mode wherein the safety shield automatically moves to a position protecting the piercing portion of the needle after the third mode.

In embodiments, the needle assembly has the following modes of operation when installed on the injection device; a first mode wherein the safety shield can move from an intermediate position to a first retracted position during injection of the piercing portion of needle into a surface so that a substance that can be suctioned into the injection device, a second mode wherein the safety shield moves to a position protecting the piercing portion of the needle after the first mode, a third mode wherein the safety shield can move to a second retracted position during injection of the piercing portion of needle into a surface which will receive the substance forced out of the injection device, and a fourth mode wherein the safety shield moves to a position protecting the piercing portion of the needle after the third mode and is prevented from moving back to a position exposing the piercing portion of the needle.

In embodiments, the needle assembly has the following modes of operation when installed on the injection device; a first mode wherein the needle assembly can be installed on the injection device, a second mode wherein the safety shield can move from an intermediate position to a first retracted position during injection of the piercing portion of needle into a surface so that a substance that can be suctioned into the injection device, a third mode wherein the safety shield moves to a position protecting the piercing portion of the needle after the second mode, a fourth mode wherein the safety shield can move to a second retracted position during injection of the piercing portion of needle into a surface which will receive the substance forced out of the injection device, and a fifth mode wherein the safety shield moves to a position protecting the piercing portion of the needle after the fourth mode and is prevented from moving back to a position exposing the piercing portion of the needle.

In embodiments, the needle assembly has the following modes of operation when installed on the injection device; a first mode wherein the needle assembly can be removably installed on the injection device, a second mode wherein the safety shield can move to a first retracted position during injection of the piercing portion of needle into a surface so that a substance that can be suctioned into the injection device, a third mode wherein the safety shield moves to a position protecting the piercing portion of the needle after the second mode, a fourth mode wherein the safety shield can move to a second retracted position during injection of the piercing portion of needle into a surface which will receive the substance forced out of the injection device, and a fifth mode wherein the safety shield moves to a position protecting the piercing portion of the needle after the fourth mode and is prevented from moving back to a position exposing the piercing portion of the needle.

In embodiments, the needle assembly has the following modes of operation when installed on the injection device; a first mode wherein the needle assembly can be installed on the injection device, a second mode wherein the safety shield can move to a first retracted position allowing injection of the piercing portion of needle, a third mode wherein the safety shield moves to a position protecting the piercing portion of the needle after the second mode, a fourth mode wherein the safety shield can move to a second retracted position allowing injection of the piercing portion of needle, and a fifth mode wherein the safety shield moves to a position protecting the piercing portion of the needle after the fourth mode and is prevented from moving back to a position exposing the piercing portion of the needle.

In embodiments, the needle assembly has the following modes of operation when installed on the injection device having the form of a syringe; a first mode wherein the needle assembly can be installed on the syringe, a second mode wherein the safety shield can move to a first retracted position allowing injection of the piercing portion of needle, and a third mode wherein the safety shield moves to a position protecting the piercing portion of the needle after the second mode and is prevented from moving back to a position exposing the piercing portion of the needle.

In embodiments, the needle assembly has the following modes of operation when installed on the injection device having the form of a syringe; a first mode wherein the needle assembly can be installed on the syringe, a second mode wherein the safety shield can move to a first retracted position allowing injection of the piercing portion of needle, and a third mode wherein the safety shield, upon triggering by a user, automatically moves to a position protecting the piercing portion of the needle after the second mode and is prevented from moving back to a position exposing the piercing portion of the needle.

In embodiments, the needle assembly has the following modes of operation when installed on the injection device having the form of a fluid collection device; a first mode wherein the needle assembly can be installed on the fluid collection device, a second mode wherein the safety shield can move to a first retracted position allowing injection of the piercing portion of needle, and a third mode wherein the safety shield moves to a position protecting the piercing portion of the needle after the second mode and is prevented from moving back to a position exposing the piercing portion of the needle.

In embodiments, the needle assembly has the following modes of operation when installed on the injection device having the form of a fluid collection device; a first mode wherein the needle assembly can be installed on the fluid collection device, a second mode wherein the safety shield can move to a first retracted position allowing injection of the piercing portion of needle, and a third mode wherein the safety shield, upon triggering by a user, automatically moves to a position protecting the piercing portion of the needle after the second mode and is prevented from moving back to a position exposing the piercing portion of the needle.

In embodiments, the assembly comprises at least one locking mechanism for non-releasably retaining the safety shield in the post use locking position.

In embodiments, the safety shield includes at least one projection that extends into a guide recess comprising at least one locking mechanism for retaining the safety shield in the post use locking position.

In embodiments, the safety shield includes at least one mechanism for preventing a locking of the safety shield when said shield in not in the post use locking position.

In embodiments, the safety shield includes at least one mechanism for providing a visual indication to the user that the needle tip has been used.

In embodiments, the assembly may further comprise a spring for biasing the safety shield away from the retracted position.

The invention also provides for a method of removing any one or more of the above-noted assemblies comprising; installing the assembly onto a proximal end of an injection device, using the assembly to inject the needle into a container containing a substance, using the assembly to inject the needle into a surface receiving the substance, and after the safety shield automatically moves to the post use locking position, removing the assembly from the injection device.

In accordance with one non-limiting aspect of the invention, there is provided a single-use needle assembly for a syringe, comprising; a body having a front portion, a back portion configured to be connected to the syringe, and a needle support arranged between the front and back portions, a hollow needle having a piercing portion projecting forwardly from the needle support, and a safety shield that is axially movable relative to the body at least between an initial position, a retracted position, and a post use locking position, wherein the needle assembly has the following modes of operation when installed on the syringe; a first mode wherein the needle assembly can be removably installed on the syringe, a second mode wherein the safety shield can move to a first retracted position during injection of the piercing portion of needle into a medicine container, and a third mode wherein the safety shield automatically moves to a position protecting the piercing portion of the needle after the second mode and is prevented from moving back to a position exposing the piercing portion of the needle.

In accordance with one non-limiting aspect of the invention, there is provided a needle assembly for a syringe, comprising a body having a front portion, a back portion configured to be connected to the syringe, and a needle support arranged between the front and back portions, a hollow needle having a piercing portion projecting forwardly from the needle support, and a safety shield that is axially movable relative to the body at least between an initial position, a retracted position, and a post use locking position. The needle assembly has the following modes of operation when installed on the syringe; a first mode wherein the safety shield can move to a first retracted position during injection of the piercing portion of needle, a second mode wherein the safety shield automatically moves to a position protecting the piercing portion of the needle after the first mode, a third mode wherein the safety shield can move to a second retracted position during injection of the piercing portion of needle, and a fourth mode wherein the safety shield automatically moves to a position protecting the piercing portion of the needle after the third mode and is prevented from moving back to a position exposing the piercing portion of the needle.

In accordance with one non-limiting aspect of the invention, there is provided a single-use needle assembly for a fluid collection device, comprising a body having a front portion, a back portion configured to be connected to the fluid collection device, and a needle support arranged between the front and back portions, a hollow needle having a piercing portion projecting forwardly from the needle support, and a safety shield that is axially movable relative to the body at least between an initial position, a retracted position, and a post use locking position. The needle assembly has the following modes of operation when installed on the syringe; a first mode wherein the needle assembly can be installed on the fluid collection device, a second mode wherein the safety shield can move to a first retracted position during injection of the piercing portion of needle, and a third mode wherein the safety shield automatically moves to a position protecting the piercing portion of the needle after the second mode and is prevented from moving back to a position exposing the piercing portion of the needle.

In accordance with one non-limiting aspect of the invention, there is provided a single-use needle assembly for a fluid collection device, comprising a body having a front portion, a back portion configured to be connected to the fluid collection device, and a needle support arranged between the front and back portions, a hollow needle having a piercing portion projecting forwardly from the needle support, and a safety shield that is axially movable relative to the body at least between an initial position, a retracted position, and a post use locking position. The needle assembly has the following modes of operation when installed on the syringe; a first mode wherein the safety shield can move to a first retracted position during injection of the piercing portion of needle, a second mode wherein the safety shield automatically moves to a position protecting the piercing portion of the needle after the first mode and is prevented from moving back to a position exposing the piercing portion of the needle, and a third mode wherein the needle assembly can be removed from the fluid collection device for safe disposal.

In accordance with one non-limiting aspect of the invention, there is provided a single-use needle assembly for a fluid collection device, comprising a body having a front portion, a back portion configured to be connected to the fluid collection device, and a needle support arranged between the front and back portions, a hollow needle having a piercing portion projecting forwardly from the needle support, and a safety shield that is axially movable relative to the body at least between an initial position, a retracted position, and a post use locking position. The needle assembly has the following modes of operation when installed on the syringe; a first mode wherein the safety shield can move to a first retracted position during injection of the piercing portion of needle, a second mode wherein the safety shield automatically moves to a position protecting the piercing portion of the needle after the first mode and is prevented from moving back to a position exposing the piercing portion of the needle, and a third mode wherein the needle assembly and the fluid collection device can be discarded while remaining connected for safe disposal.

In accordance with one non-limiting aspect of the invention, there is provided a needle assembly for a fluid collection device, comprising a body having a front portion, a back portion configured to be connected to the fluid collection device, and a needle support arranged between the front and back portions, a hollow needle having a piercing portion projecting forwardly from the needle support, and a safety shield that is axially movable relative to the body at least between an initial position, a retracted position, and a post use locking position. The needle assembly has the following modes of operation when installed on the fluid collection device; a first mode wherein the safety shield can move to a first retracted position during injection of the piercing portion of needle and a second mode wherein the safety shield automatically moves to a position protecting the piercing portion of the needle after the first mode and is prevented from moving back to a position exposing the piercing portion of the needle.

In accordance with one non-limiting aspect of the invention, there is provided a single-use needle assembly for a syringe, comprising a body having a front portion, a back portion configured to be connected to the fluid collection device, and a needle support arranged between the front and back portions, a hollow needle having a piercing portion projecting forwardly from the needle support, and a safety shield that is axially movable relative to the body at least between an initial position, a retracted position, and a post use locking position. The needle assembly has the following modes of operation when installed on the syringe; a first mode wherein the safety shield can move to a first retracted position during injection of the piercing portion of needle, a second mode wherein the safety shield automatically moves to a position protecting the piercing portion of the needle after the first mode and is prevented from moving back to a position exposing the piercing portion of the needle, and a third mode wherein the needle assembly can be removed from the syringe for safe disposal.

In accordance with one non-limiting aspect of the invention, there is provided a needle assembly for a syringe, comprising a body having a front portion, a back portion configured to be connected to the fluid collection device, and a needle support arranged between the front and back portions, a hollow needle having a piercing portion projecting forwardly from the needle support, and a safety shield that is axially movable relative to the body at least between an initial position, a retracted position, and a post use locking position. The needle assembly has the following modes of operation when installed on the syringe; a first mode wherein the safety shield can move to a first retracted position during injection of the piercing portion of needle, a second mode wherein the safety shield automatically moves to a position protecting the piercing portion of the needle after the first mode, a third mode wherein the safety shield can move to a second retracted position during injection of the piercing portion of needle, a fourth mode wherein the safety shield automatically moves to a position protecting the piercing portion of the needle after the third mode and is prevented from moving back to a position exposing the piercing portion of the needle, and a fifth mode wherein the needle assembly can be removed from the syringe for safe disposal.

In accordance with one non-limiting aspect of the invention, there is provided a needle assembly for a syringe, comprising a body having a front portion, a back portion configured to be connected to the fluid collection device, and a needle support arranged between the front and back portions, a hollow needle having a piercing portion projecting forwardly from the needle support, and a safety shield that is axially movable relative to the body at least between an initial position, a retracted position, and a post use locking position. The needle assembly has the following modes of operation when installed on the syringe; a first mode wherein the needle assembly can be removably installed on the syringe, a second mode wherein the safety shield can move to a first retracted position during injection of the piercing portion of needle, a third mode wherein the safety shield automatically moves to a position protecting the piercing portion of the needle after the second mode, a fourth mode wherein the safety shield can move to a second retracted position during injection of the piercing portion of needle, a fifth mode wherein the safety shield automatically moves to a position protecting the piercing portion of the needle after the fourth mode and is prevented from moving back to a position exposing the piercing portion of the needle, and a fifth mode wherein the needle assembly can be removed from the syringe for safe disposal.

In accordance with one non-limiting aspect of the invention, there is provided a needle assembly for an injection device comprising an assembly of anyone of the types disclosed in US 2011/0160675 with the exception that the pen needle interface and rear facing needle which is replaced with a standard interface of the type shown herein so that the needle assembly can be utilized on a syringe or a fluid collection device.

In accordance with one non-limiting aspect of the invention, there is provided a needle assembly for an injection device comprising an assembly of anyone of the types disclosed in US 2011/0160675 with the exception that the pen needle interface and rear facing needle which is modified for use on a fluid collection device.

In accordance with one non-limiting aspect of the invention, there is provided a needle assembly for an injection device comprising an assembly of anyone of the types disclosed in US 2011/0257603 with the exception that the pen needle interface and rear facing needle which is replaced with a standard interface of the type shown herein so that the needle assembly can be utilized on a syringe or a fluid collection device.

In accordance with one non-limiting aspect of the invention, there is provided a needle assembly for an injection device comprising an assembly of anyone of the types disclosed in US 2011/0257603 with the exception that the pen needle interface, rear facing needle and rear safety device which is modified for use on a fluid collection device.

In accordance with one non-limiting aspect of the invention, there is provided a needle assembly for an injection device comprising an assembly of anyone of the types disclosed in US 2011/0288491 with the exception that the pen needle interface and rear facing needle which is replaced with a standard interface of the type shown herein so that the needle assembly can be utilized on a syringe or a fluid collection device.

In accordance with one non-limiting aspect of the invention, there is provided a needle assembly for an injection device comprising an assembly of anyone of the types disclosed in US 2011/0288491 with the exception that the pen needle interface, rear facing needle and rear safety device which is modified for use on a fluid collection device.

In accordance with one non-limiting aspect of the invention, there is provided a syringe system comprising rat least first and second needle assemblies each comprising a common interface and each including a body having a front portion, a back portion configured to be connected to the fluid collection device, and a needle support arranged between the front and back portions, a needle having a piercing portion projecting forwardly from the needle support, and a safety shield that is axially movable relative to the body at least between an initial position and a retracted position.

In embodiments, the needle of the first needle assembly is larger in at least one of a length and a diameter or gauge than a needle of the second needle assembly.

In embodiments, the needle of the first needle assembly is larger in both a length and a diameter or gauge than a needle of the second needle assembly.

In embodiments, the first needle assembly is a single-use needle assembly.

In embodiments, the first and second needle assemblies are each single-use needle assemblies.

In embodiments, the system has the following modes of operation; a first mode wherein the first needle assembly is installed on the syringe, a second mode wherein the safety shield of the first needle assembly can move to a first retracted position during injection of the piercing portion of needle into a container containing a substance that can be suctioned into the syringe, a third mode wherein first needle assembly is removed from the syringe, a fourth mode wherein the second needle assembly is installed on the syringe and a fifth mode wherein the safety shield of the second needle assembly can move to a first retracted position during injection of the piercing portion of needle into a surface which will receive the substance from the syringe.

In embodiments, the system may further comprise a sixth mode wherein a plunger of the syringe is broken off while a piston of the syringe remains inside a barrel of the syringe.

In embodiments, the safety shield of each of the first and second needle assemblies are locked respectively after the second and fifth modes.

In embodiments, the first and second needle assemblies comprise single-use needle assemblies.

In embodiments, the first and second needle assemblies comprise different single-use needle assemblies.

In accordance with one non-limiting aspect of the invention, there is provided a needle assembly having the following modes of operation when installed on an injection device; a first mode wherein the safety shield can move to a first retracted position allowing injection of the piercing portion of needle from a position at least partially covering the piercing portion of the needle and a second mode wherein the safety shield moves to a position protecting the piercing portion of the needle after the first mode and is prevented from moving back to a position exposing the piercing portion of the needle.

In accordance with one non-limiting aspect of the invention, there is provided a needle assembly having the following modes of operation when installed on an injection device; a first mode wherein the safety shield can move to a first retracted position allowing injection of the piercing portion of needle from a position completely covering the piercing portion of the needle and a second mode wherein the safety shield moves to a position protecting the piercing portion of the needle after the first mode and is prevented from moving back to a position exposing the piercing portion of the needle.

In accordance with one non-limiting aspect of the invention, there is provided a spike needle assembly comprising a body having a connectable back portion, a needle having a piercing portion projecting forwardly from the body, and a safety shield that is movable at least between an initial position, at least a partially retracted position, and a post use locking position.

In embodiments, the connectable back portion is adapted to be connected to tubing.

In embodiments, the connectable back portion is adapted to be connected to a fluid delivery device.

In accordance with one non-limiting aspect of the invention, there is provided a needle assembly for a medical device, comprising the following modes of operation; a first mode wherein a safety shield of the needle assembly can move at least axially to a first retracted position exposing a piercing portion of a needle, a second mode wherein the safety shield can move at least axially to an extended position covering the piercing portion of needle, a third mode wherein the safety shield of the needle assembly can move at least axially to a second retracted position exposing a piercing portion of a needle only upon selection or activation by a user, and a fourth mode wherein the safety shield of the needle assembly can move at least axially to an extended position covering the piercing portion of a needle.

In accordance with one non-limiting aspect of the invention, there is provided a assembly for a medical device, comprising the following modes of operation; a first mode wherein a safety shield of the needle assembly can move at least axially to a first retracted position exposing a piercing portion of a needle, a second mode wherein the safety shield can move at least axially to an extended position covering the piercing portion of needle, a third mode wherein the safety shield of the needle assembly can move at least axially to a second retracted position exposing a piercing portion of a needle only upon selection or activation by a user, and a fourth mode wherein the safety shield of the needle assembly is moved at least axially to a non-releasably locked position covering the piercing portion of a needle.

In accordance with one non-limiting aspect of the invention, there is provided a needle assembly for a medical device, comprising the following modes of operation; a first mode wherein a safety shield of the needle assembly can move at least axially to a retracted position exposing a piercing portion of a needle, a second mode wherein the safety shield can move at least axially to an extended position covering the piercing portion of needle, a third mode wherein the safety shield of the needle assembly can move at least axially to a retracted position exposing a piercing portion of a needle only upon at least partial rotation of the safety shield, and a fourth mode wherein the safety shield of the needle assembly is moved at least axially to a non-releasably locked position covering the piercing portion of a needle.

In accordance with one non-limiting aspect of the invention, there is provided a needle assembly for a medical device, comprising the following modes of operation; a first mode wherein a safety shield of the needle assembly can move at least axially to a retracted position exposing a piercing portion of a needle, a second mode wherein the safety shield can move at least axially to an extended position covering the piercing portion of needle and is releasably retained therein, a third mode wherein the safety shield of the needle assembly can move at least axially to a retracted position exposing a piercing portion of a needle, and a fourth mode wherein the safety shield of the needle assembly is moved at least axially to a non-releasably locked position covering the piercing portion of a needle.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

In FIG. 30, the shield is in a second extended or needle covering position;

DETAILED DESCRIPTION OF THE INVENTION

Figure 1:
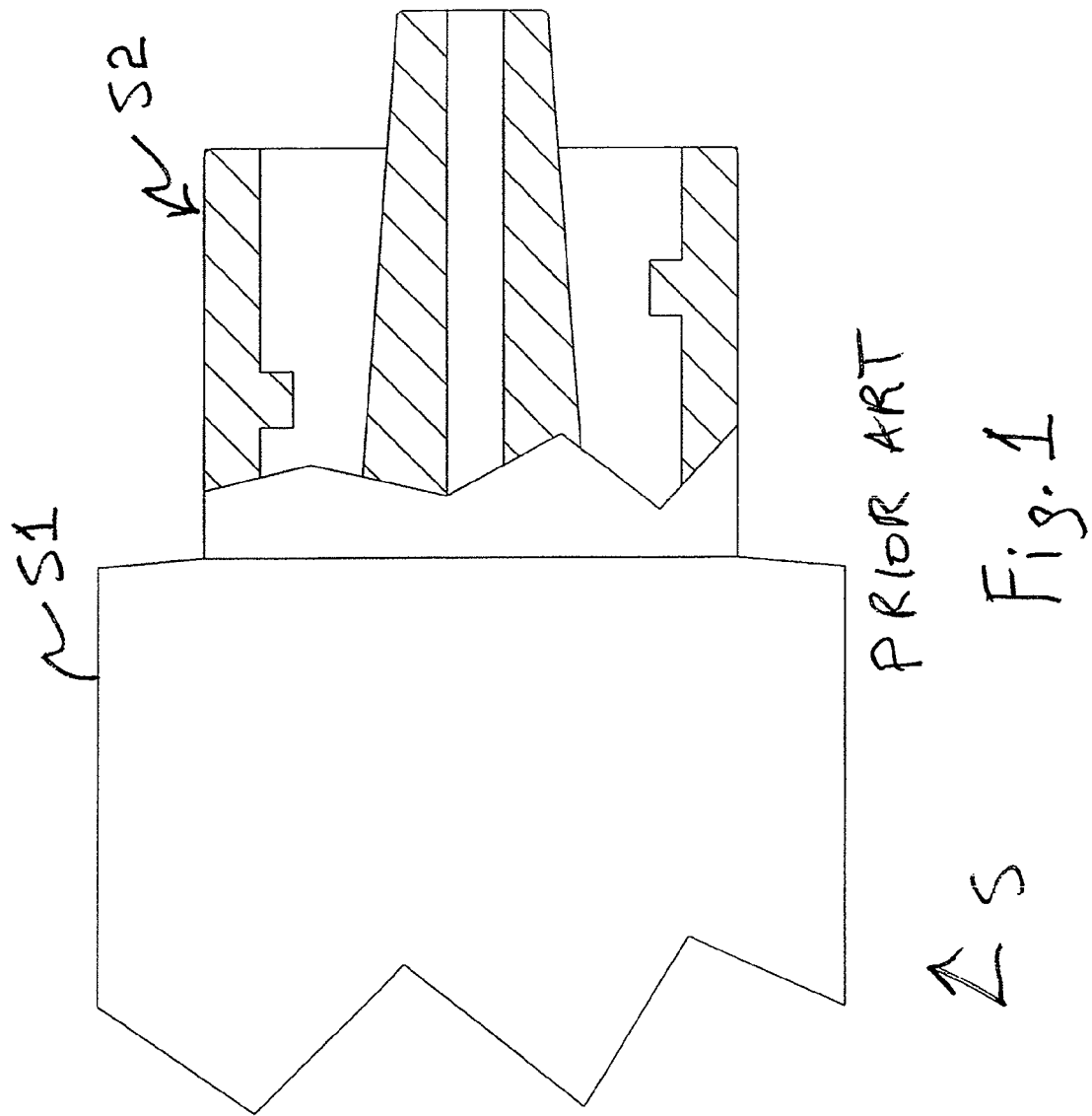
FIG. 1 shows an enlarged partial side cross-section view of a front portion of a standard or known syringe which can be used with the invention. The syringe has a luer-lok type interface. The plunger and piston are not shown.

FIG. 1 shows a partial view of a luer-lock type interface of a syringe S that can be used to practice one or more non-limiting embodiments of the invention. The syringe S includes a syringe body S1 and a standard interface or luer-lock type connecting interface S2. As the art of syringes or injections devices is vast and known, additional details are not herein provided regarding these features. However, the knowledge of such devices can advantageously be utilized to practice aspects of the invention.

Figure 2:
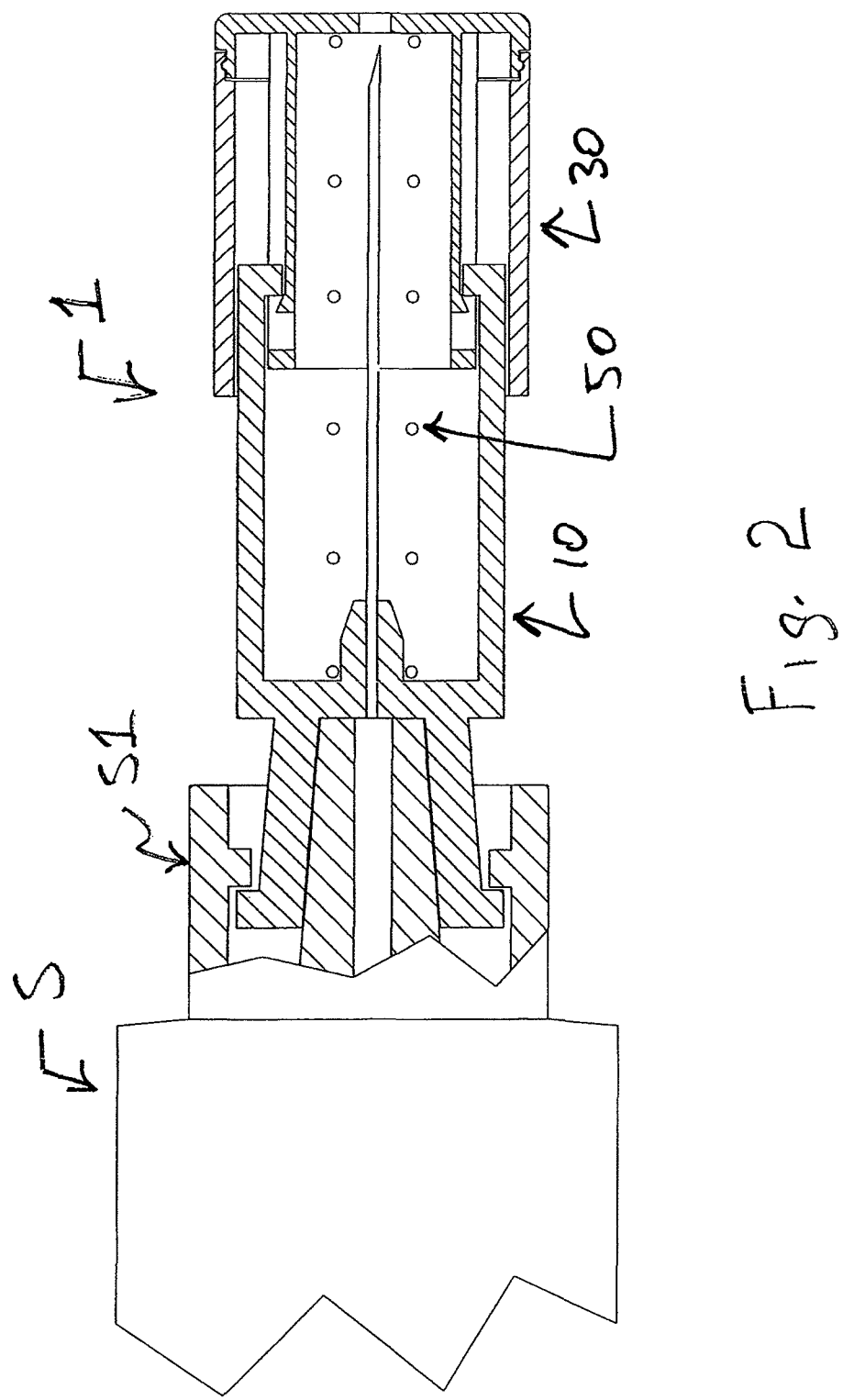
FIG. 2 shows a side-cross-section view of a needle assembly mounted to the syringe of FIG. 1 in accordance with one non-limiting embodiment of the invention. The shield of needle assembly is shown in an initial, intermediate, or prior-use configuration. A packaging needle cover (not shown but similar to that shown in FIG. 26) is removed from the same.
Figure 3:
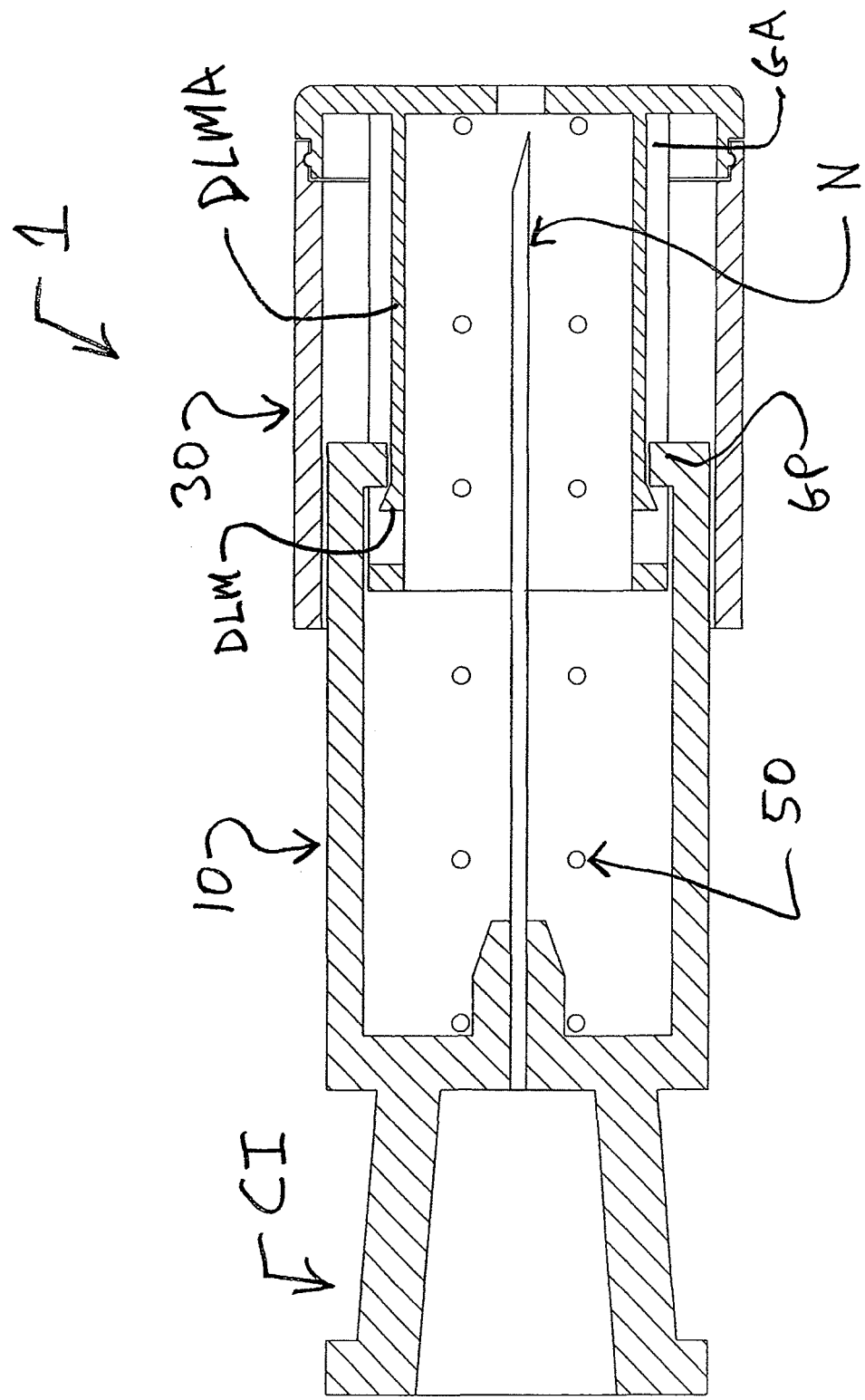
FIG. 3 shows the needle assembly of FIG. 2 prior to being installed on the syringe of FIG. 1.

FIGS. 2-5 show a needle assembly 1 mounted to the syringe of FIG. 1 in accordance with one non-limiting embodiment of the invention. The assembly 1 includes a body 10, a needle N, a needle shield 30 and a spring 50. In FIG. 2, the needle assembly 1 is shown in an initial, intermediate, or prior-use configuration. Although not shown, a packaging needle cover (similar to that shown in FIG. 26) can be removably mounted to the same. Another cap (not shown) can be arranged to cover the connecting interface CI. Additionally or alternatively, the device of FIG. 2 (or that shown in FIG. 26) can be packaged in the form shown. FIG. 3 shows the needle assembly of FIG. 2 prior to being installed on the syringe of FIG. 1. As is apparent from FIG. 3, the assembly 1 can be connected to the syringe interface S2 via the connecting interface CI portion of the body 10. This standard interface CI will be complementary to that of the interface S2 such that if the interface S2 is, by way of example, a female luer-lock type interface, then the distal interface CI should be a male luer-lock type interface so as to properly and sealingly connected thereto. In embodiment, this connection is a removable or releasable connection.

Figure 4:
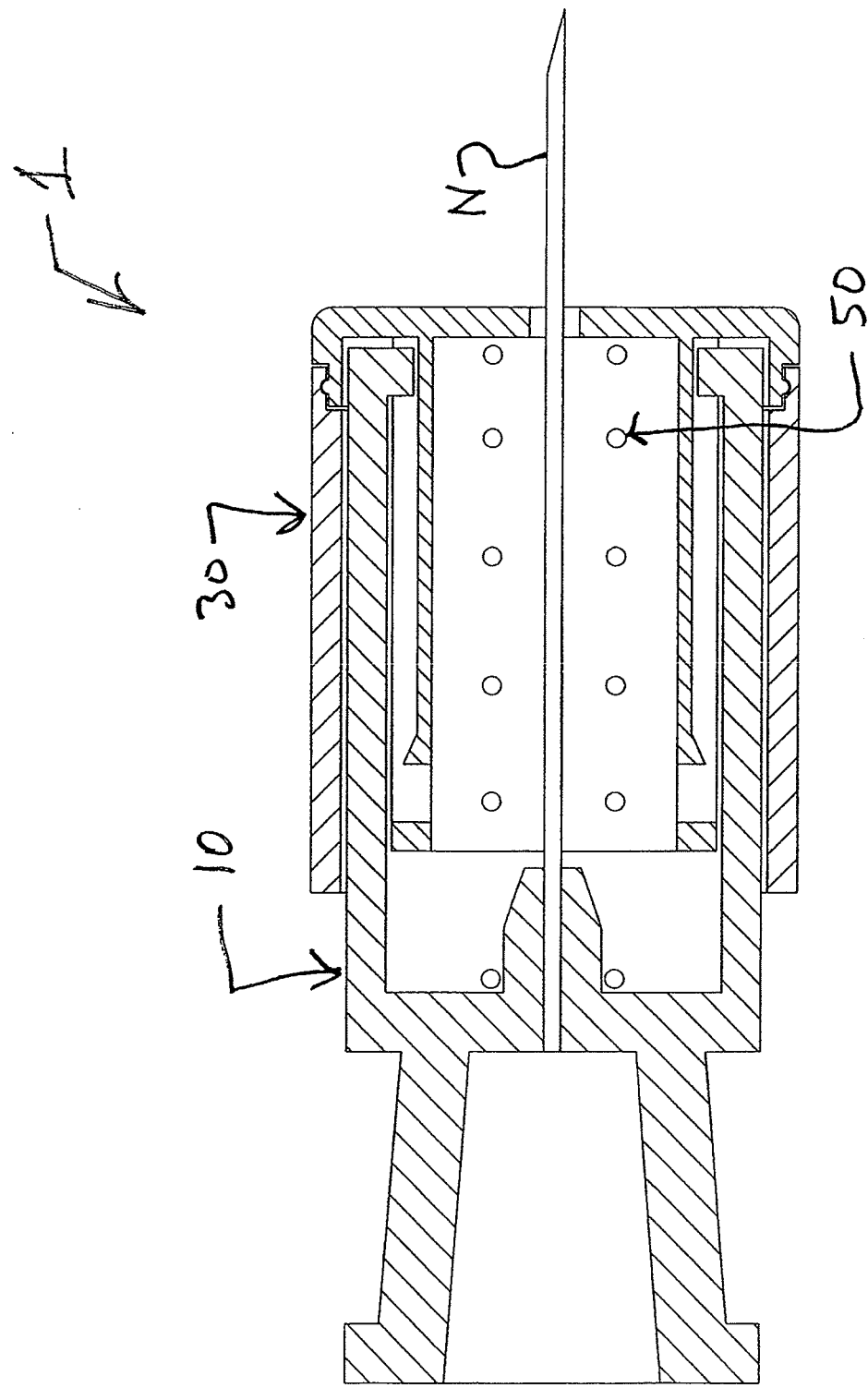
FIG. 4 shows the needle assembly of FIG. 3 in an injection position, i.e., a position wherein the shield is retracted so that the piercing portion of the needle can pierce a surface. In this position, when installed on a syringe, the needle can be used to withdraw a fluid into the syringe or inject a substance in the syringe.
Figure 5:
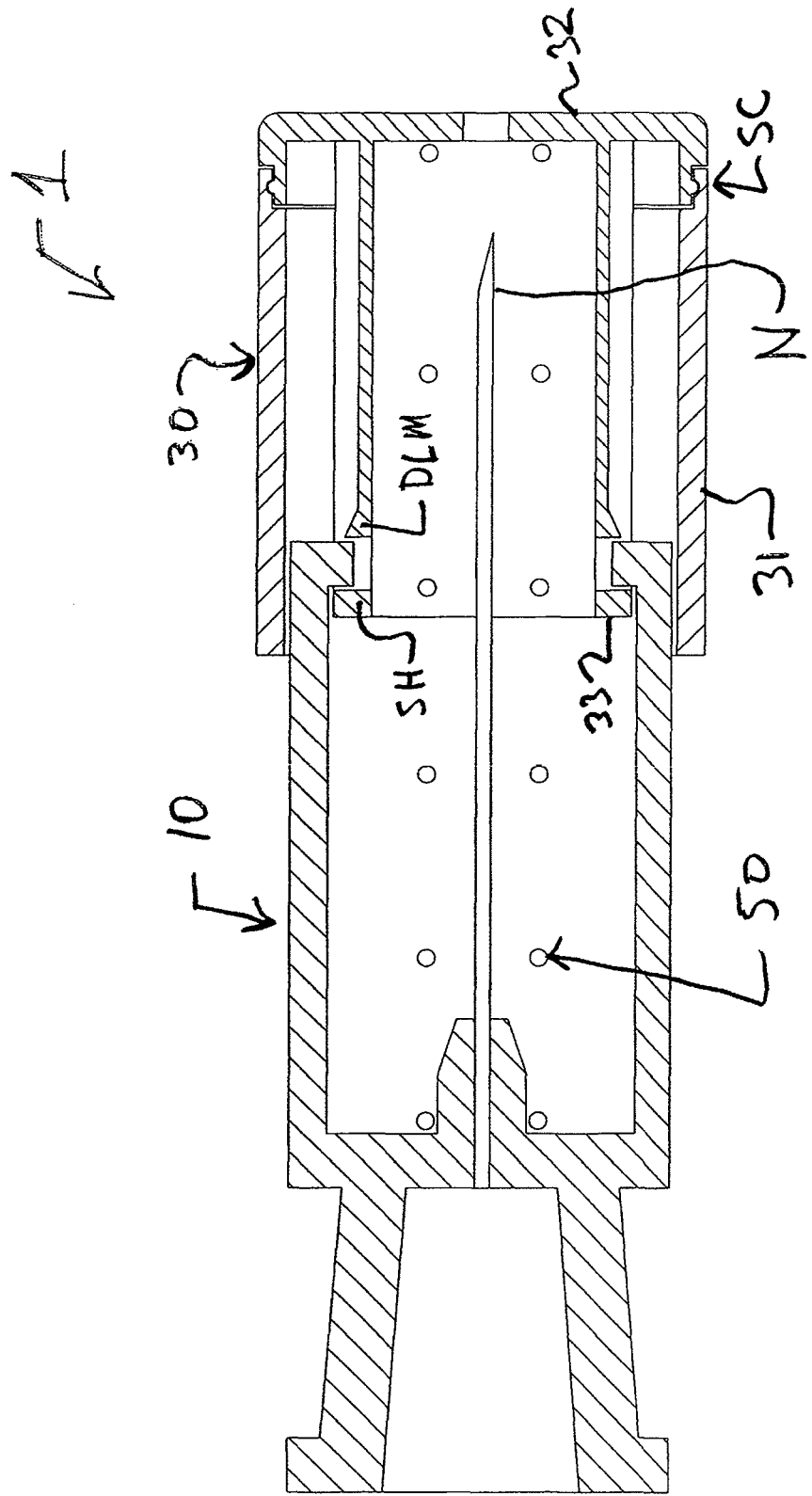
FIG. 5 shows a needle assembly of FIG. 4 after the needle shield is automatically moved by a spring to the non-releasably locked position. In this position, the needle assembly is rendered unusable and can be safely disposed of. The needle shield is thus prevented from moving back by an amount sufficient to allow exposure to the piercing portion of the needle.

FIG. 4 shows the needle assembly of FIG. 3 in an injection position, i.e., a position wherein the shield 30 is axially retracted against the biasing force of the spring 50 so that the piercing, proximal or free end portion of the needle N can pierce a surface, e.g., skin, tissue, medicine container, etc. In this position, when installed on a syringe S, the needle N can be used to withdraw a fluid into the syringe S or inject a substance already within the syringe S. FIG. 5 shows a needle assembly 1 of FIG. 4 after the needle shield 30 is automatically moved by the spring 50 to the non-releasably locked position. In this position, the needle assembly 1 is rendered unusable and can be safely disposed of. The needle shield 30 is thus prevented from moving axially back by an amount sufficient to allow exposure to the piercing portion of the needle N.

To understand how the shield 30 can become locked in the position shown in FIG. 5, one should compare FIG. 3 to FIG. 5 and see how the needle shield 30 is axially retained in an intermediate position between FIG. 5 and FIG. 4. This position is maintained by the biasing force of the spring 50 causing a tapered surface of one or more delectable locking mechanisms DLM of the shield 30 to engage or contact one or more guiding projections GP of the body 10. Each guiding projection GP is guided within a respective guiding arrangement GA, e.g., a guiding groove, formed in the shield 30. This sliding engagement between the guiding projections GP and the guiding recesses GA allows the shield 30 to move axially or be guided axially relative to the body 10 without also rotating relative thereto. When, however, the shield 30 is moved back to the position shown in FIG. 4 and released, the spring 50 develops sufficient expansion force to overcome the engagement shown in FIG. 3. Although this occurs quickly (in a fraction of a second), what happens is that when the tapered surface of the deflectable locking member DLM contacts the projection GP, it is deflected inwardly thereby until the deflectable locking member DLM actually moves past the projection GP whereupon it deflects outwardly again. This movement occurs because each delectable locking member DLM is coupled to a delectable arm DLMA which functions like a leaf spring. Once the member DLM moves axially past the projection GP along the proximal direction and assumes an relaxed position shown in FIG. 5, the shield 30 becomes non-releasably or permanently locked to the body 10 such that it cannot move back to the position shown in either FIG. 3 or FIG. 4. If the user tries to move the shield 30 axially back to again compress the spring 50, each member DLM contacts a respective projection GP which prevents further movement. Moreover, as each guiding recess GA extends only up to a stop shoulder SH, the shield 30 becomes axially retained by the engagement between the projection GP and elements SH and DLM. Furthermore, because elements GP, SH and DLM are arranged on an inner sleeve portion 33 which is concealed within an outer sleeve portion 31 and an annular face portion 32, the user cannot deactivate the locking system without destroying the assembly 1.

Figure 36:
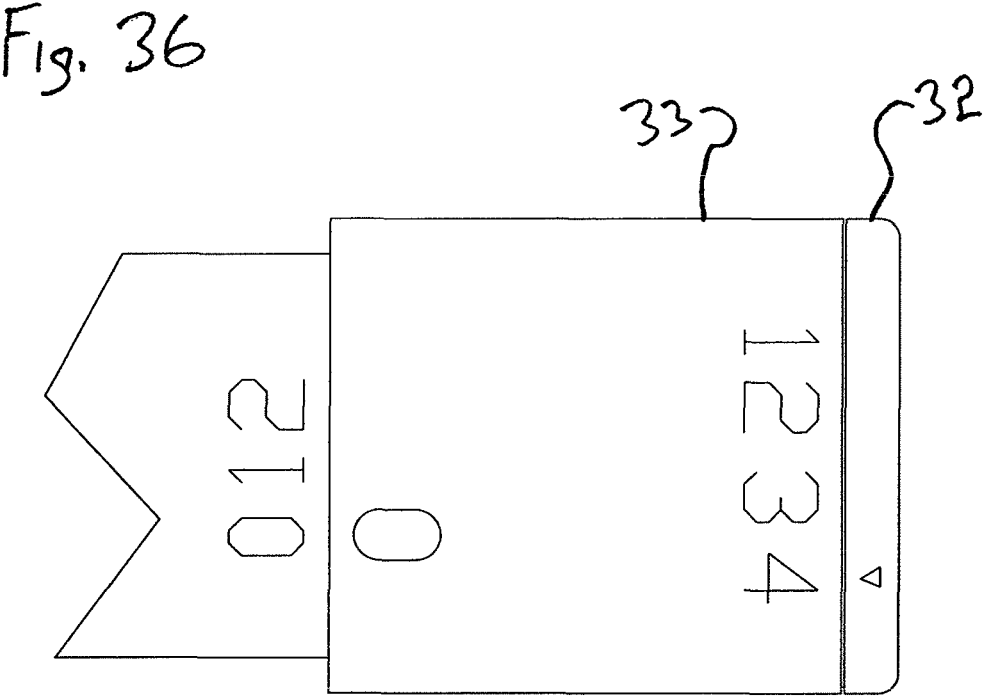
FIGS. 36 and 37 show one way in which one or more of the herein disclosed embodiments can utilize depth of penetration adjustment.
Figure 37:
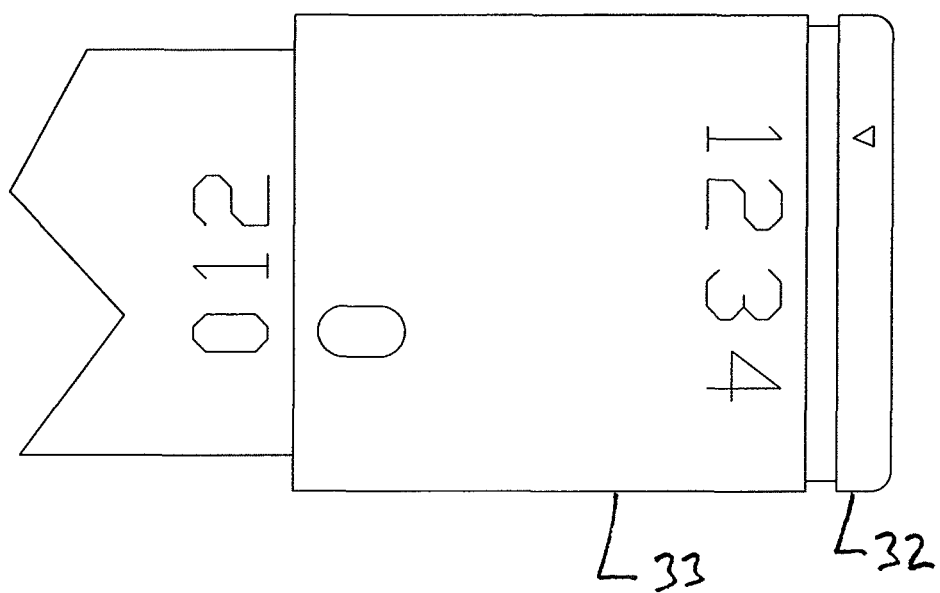

To facilitate assembly of the device 1, the needle shield 30 can be made of, e.g., two components as shown in FIG. 5. These include the outer sleeve component portion 31 and another component including the face portion 32 and inner sleeve portion 33. These components can be non-releasably connected to one another via, e.g., a non-releasable snap connection SC. Other connections can also be utilized such as threads, adhesives, etc. Still further, a threaded connection between these two components can also be utilized to provide the device with depth of penetration adjustment as shown in FIGS. 36 and 37. Indicia and an indicator can also be used on the two component parts 32 and 33 making up the needle shield to provide the user with an indicator of depth of penetration setting (see FIGS. 36 and 37).

The embodiment shown in FIGS. 2-5 can thus have the form of needle assembly 1 that utilizes a body 10 having a front portion, a back portion CI configured to be connected to device S configured to inject or withdraw fluids, and a wall or needle support separating the front and back portions (see FIG. 3). A needle N has a piercing portion projecting forwardly from the wall or needle support. A safety shield 30 is axially movable relative to the body 10 at least between an initial position (FIG. 3), at least partially retracted position (FIG. 4), and a post use locking or locked position (FIG. 5). The safety shield 30 at least one of: is at least partially disposed within the front portion of the body 10, includes a locking system DLM/GP which is prevented from being contacted by a user's fingers, and moves linearly without also rotating. Additionally or alternatively, the shield 30 includes at least one mechanism DLM for preventing a locking of the safety shield 30 when said shield in not in the post use locking position. Additionally or alternatively, the shield 30 includes a first portion 33 that is at least partially disposed within the front portion of the body 10, a second portion 31 that at least partially covers the front portion, and has its movement limited by engagement between at least one projection GP extending into a guide recess GA.

Figure 6:
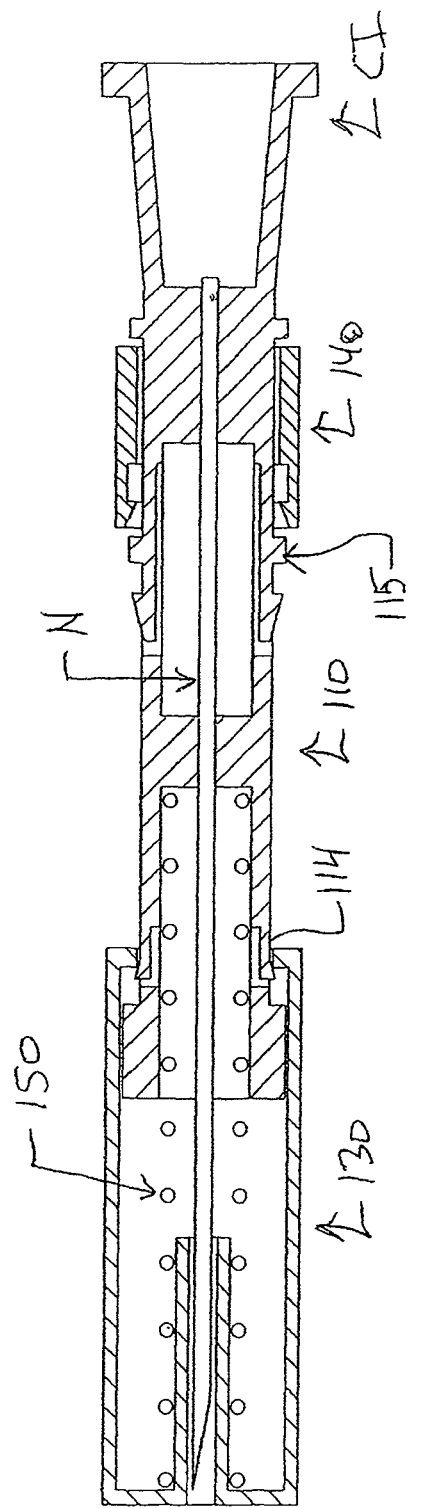
FIG. 6 shows a side cross-section view of a known needle assembly which can be used in accordance with another embodiment of the invention.

FIG. 6 shows a needle assembly disclosed in US 2010/0286611 to SCHRAGA which is herein expressly incorporated by reference in its entirety and which can be used in accordance with another embodiment of the invention. In this embodiment, the assembly 100 can be installed on an injection device or syringe S of FIG. 1 and includes a body 110, a needle shield 130, a spring 150, a needle N, a trigger sleeve 140, deflectable locking members 114 and a standard connecting interface CI. An advantage of this embodiment relates to the fact that the needle shield 130 can be releasably retained in the retracted position and does not automatically move to the locked fully extended position until the user moves the trigger sleeve 140 into engagement with projections 115 to cause release of the locking engagement between the body 110 and the needle shield 130.

Figure 7:
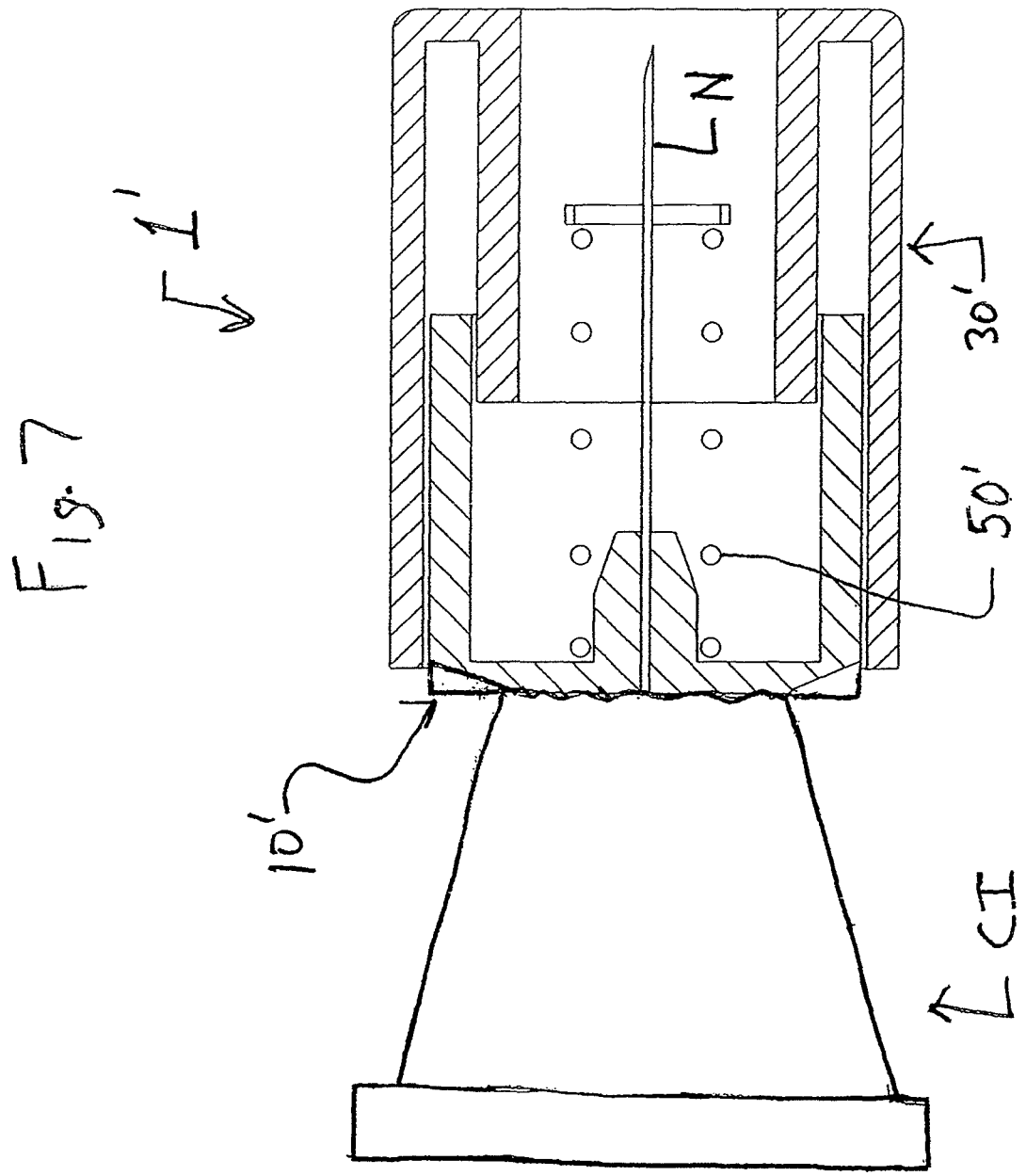
FIG. 7 shows a side partial cross-section view of a needle assembly in accordance with another embodiment of the invention. The shield of needle assembly is shown in an initial, intermediate, or prior-use configuration. A packaging needle cover (not shown but similar to that shown in FIG. 26) removed from the same.
Figure 8:
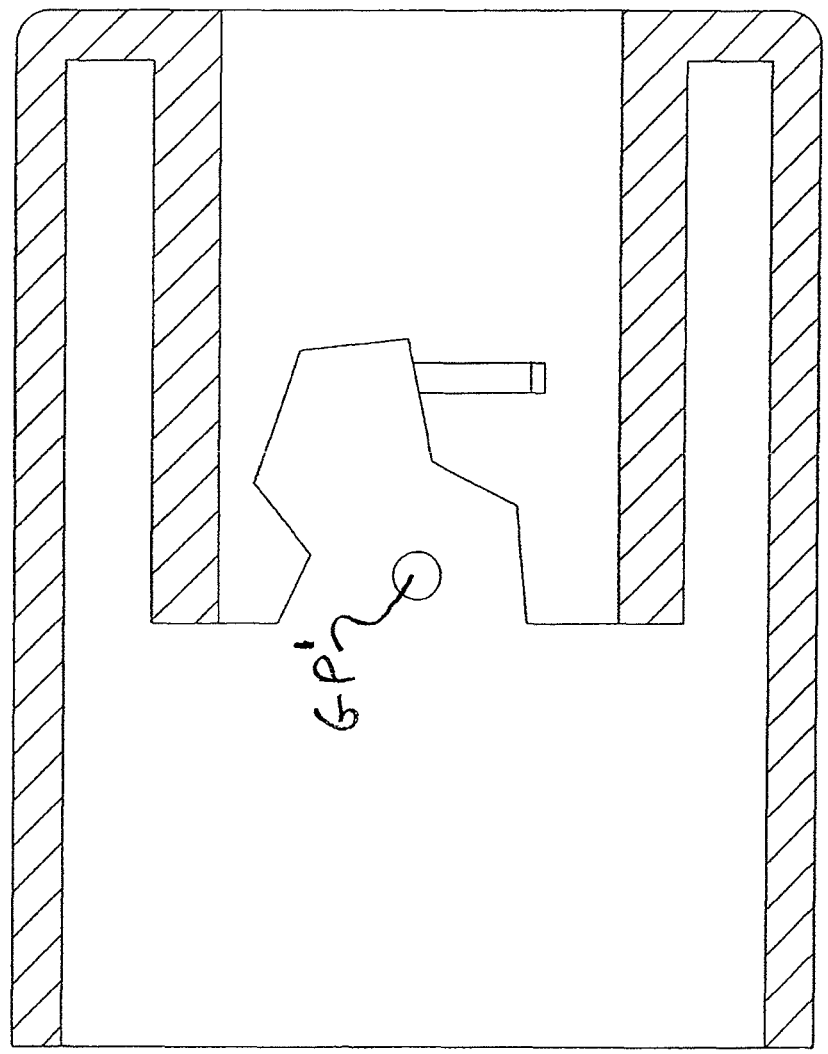
FIG. 8 shows the needle shield used on the needle assembly of FIG. 7.
Figure 9:
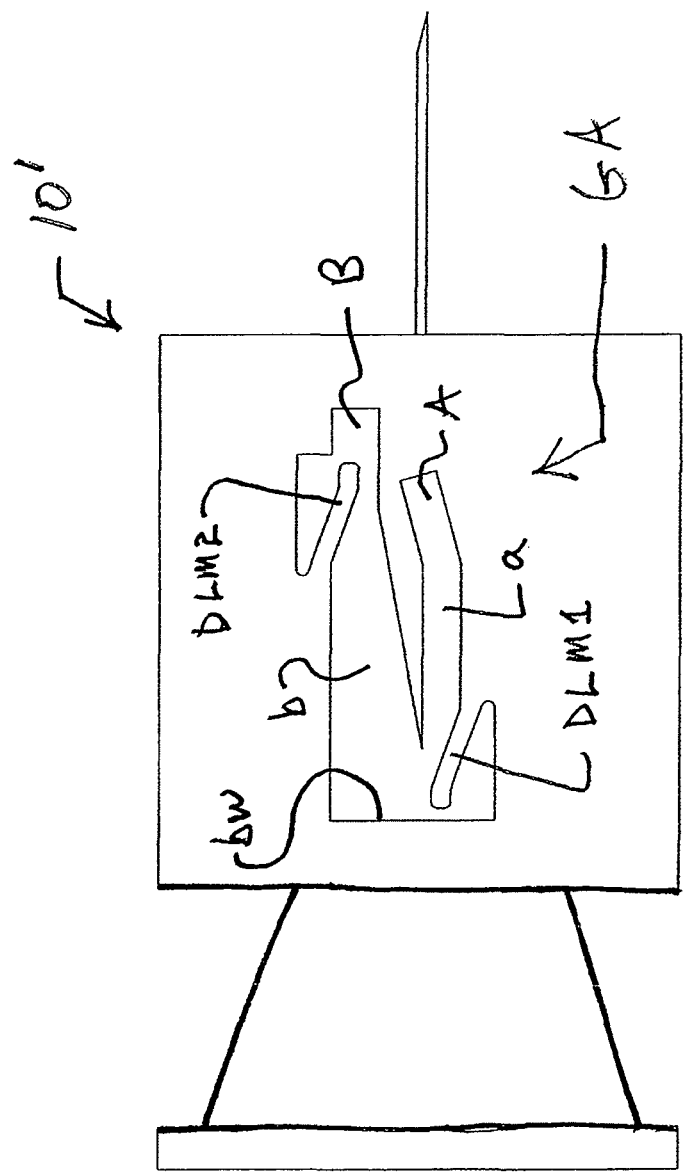
FIG. 9 shows the body used on the needle assembly of FIG. 7.

FIGS. 7-9 show a needle assembly 1' in accordance with another embodiment of the invention. The assembly 1' includes a body 10', a needle N, a needle shield 30' and a spring 50'. In FIG. 7, the needle assembly 1' is shown in an initial, intermediate, or prior-use configuration. Although not shown, a packaging needle cover (similar to that shown in FIG. 26) can be removably mounted to the same. FIG. 8 shows the needle shield 30' used on the needle assembly of FIG. 7 and show the location of at least one inward facing guiding projection GP' which is configured to move within at least one external guiding recess formed on the body 10' shown in FIG. 9.

The device shown in FIGS. 7-9 can function as follows with reference to FIG. 9. After the assembly 1' is installed on the injection device S; a first mode includes moving the safety shield 30' from the position shown in FIG. 7 to a first retracted position during injection of the piercing portion of needle N into a surface, e.g., into a container containing a substance that can be suctioned into the injection device. When this happens, the guiding projection GP' moves from position A in guide recess portion "a" of a complex cam guiding recess arrangement until it contacts and deflects out of the way deflectable locking member DLM1. Once it enters portion "b" and contacts the bottom wall bw, the deflectable locking member DLM1 will move back to the relaxed position shown in FIG. 9 and function to prevent the guiding projection GP' from moving back into the recess portion "a". A second mode results when the safety shield 30' automatically moves to a position protecting the piercing portion of the needle N after the first mode. When this happens, the guiding projection GP' moves from position adjacent the wall bw in guide recess portion "b" until it contacts and deflects out of the way deflectable locking member DLM2. Once it enters portion or position "B", the deflectable locking member DLM2 will move back to the relaxed position shown in FIG. 9 and functions to prevent the guiding projection GP' from moving back into the recess portion "b". At this point, the needle shield 30' has become locked in the fully extended or needle covering position. It cannot be moved backwards or distally as it is prevented from doing so by the member DLM2 and also cannot move forward as it contacts a wall defining the space or position B. The user has no choice by to discard the assembly 1' after it is used a single time and this can be done safely as the needle N is fully covered and protected by the needle shield 30'. When the needle shield 30' moves from the initial position A to the final locked position B, the needle shield 30' experiences both backward and forward axial movement, but also rotation relative to the body 10'.

Figure 10:
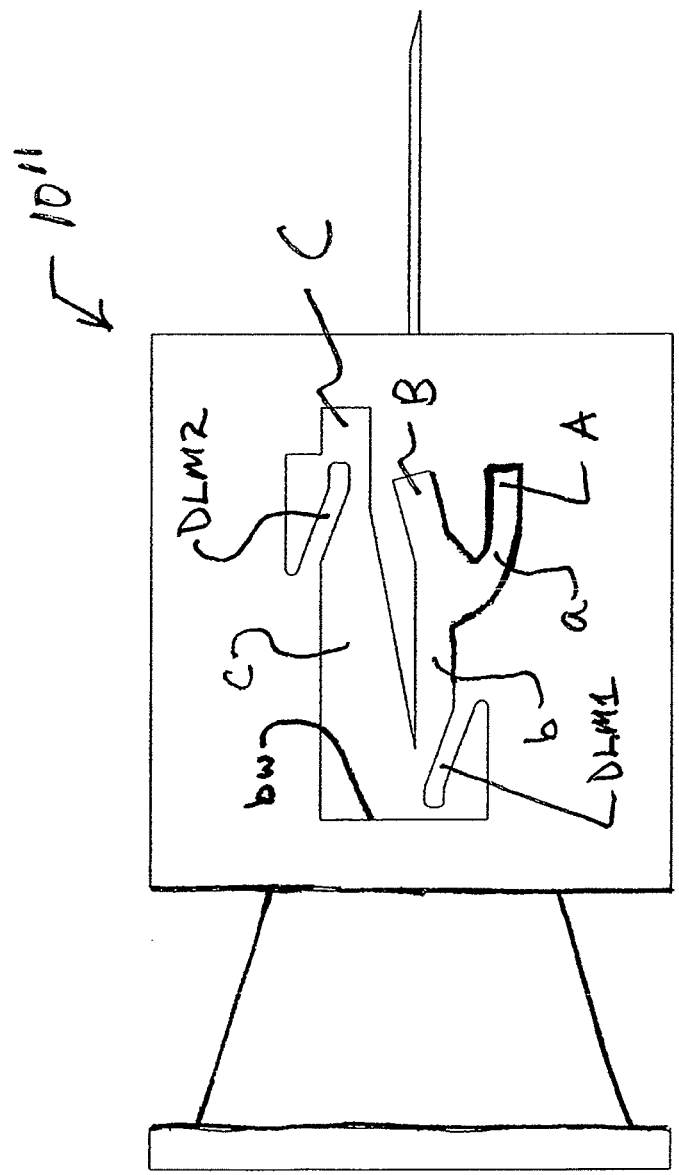
FIG. 10 shows an alternative body which can be used on the needle assembly of FIG. 7.

The device shown in FIG. 7 can also be modified so that the body shown in FIG. 9 is replaced with that shown in FIG. 10. After the assembly is installed on the injection device S; a first mode includes moving the safety shield from the position shown in FIG. 7 to a first retracted position during injection of the piercing portion of needle N into a surface, e.g., into a container containing a substance that can be suctioned into the injection device. When this happens, the guiding projection moves from position A in guide recess portion "a" until it contacts but does not deflect out of the way deflectable locking member DLM1. This allows the user to only partially expose the needle N if desired. Once it enters portion "b" and contacts the member DLM1, if the user then releases of the needle shield, it will move under the action of the spring to position B. Furthermore, with this arrangement, the user can make a further injection. When this happens, the guiding projection moves from position B in guide recess portion "b" until it contacts and deflects out of the way deflectable locking member DLM1. Once it enters portion "c" and contacts the bottom wall bw, the deflectable locking member DLM1 will move back to the relaxed position shown in FIG. 10 and function to prevent the guiding projection from moving back into the recess portion "b". A third mode results when the safety shield automatically moves to a position protecting the piercing portion of the needle N after the second mode. When this happens, the guiding projection moves from position adjacent the wall bw in guide recess portion "c" until it contacts and deflects out of the way deflectable locking member DLM2. Once it enters portion or position "C", the deflectable locking member DLM2 will move back to the relaxed position shown in FIG. 10 and functions to prevent the guiding projection from moving back into the recess portion "c". At this point, the needle shield has become locked in the fully extended or needle covering position. It cannot be moved backwards or distally as it is prevented from doing so by the member DLM2 and also cannot move forward as it contacts a wall defining the space or position C. The user has no choice by to discard the assembly after it is used a couple of times and this can be done safely as the needle N is fully covered and protected by the needle shield. When the needle shield moves from the initial position A to the final locked position C, the needle shield experiences both backward and forward axial movement, but also rotation relative to the body 10".

Figure 11:
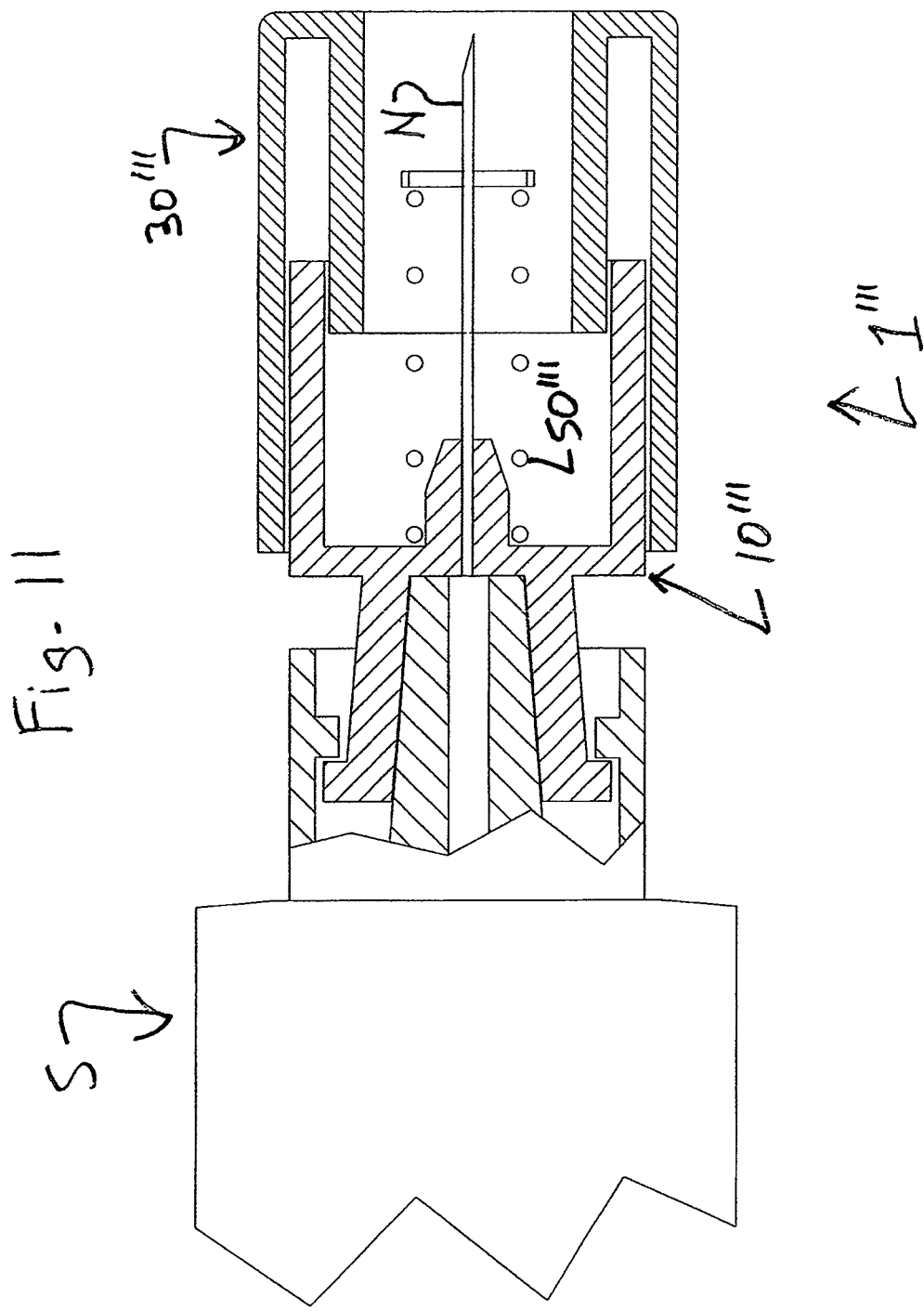
FIG. 11 shows a side cross-section view of needle assembly mounted to the syringe of FIG. 1 in accordance with another non-limiting embodiment of the invention. The shield of needle assembly is shown in an initial, intermediate, or prior-use configuration. A packaging needle cover (not shown but similar to that shown in FIG. 26) is removed from the same.
Figure 12:
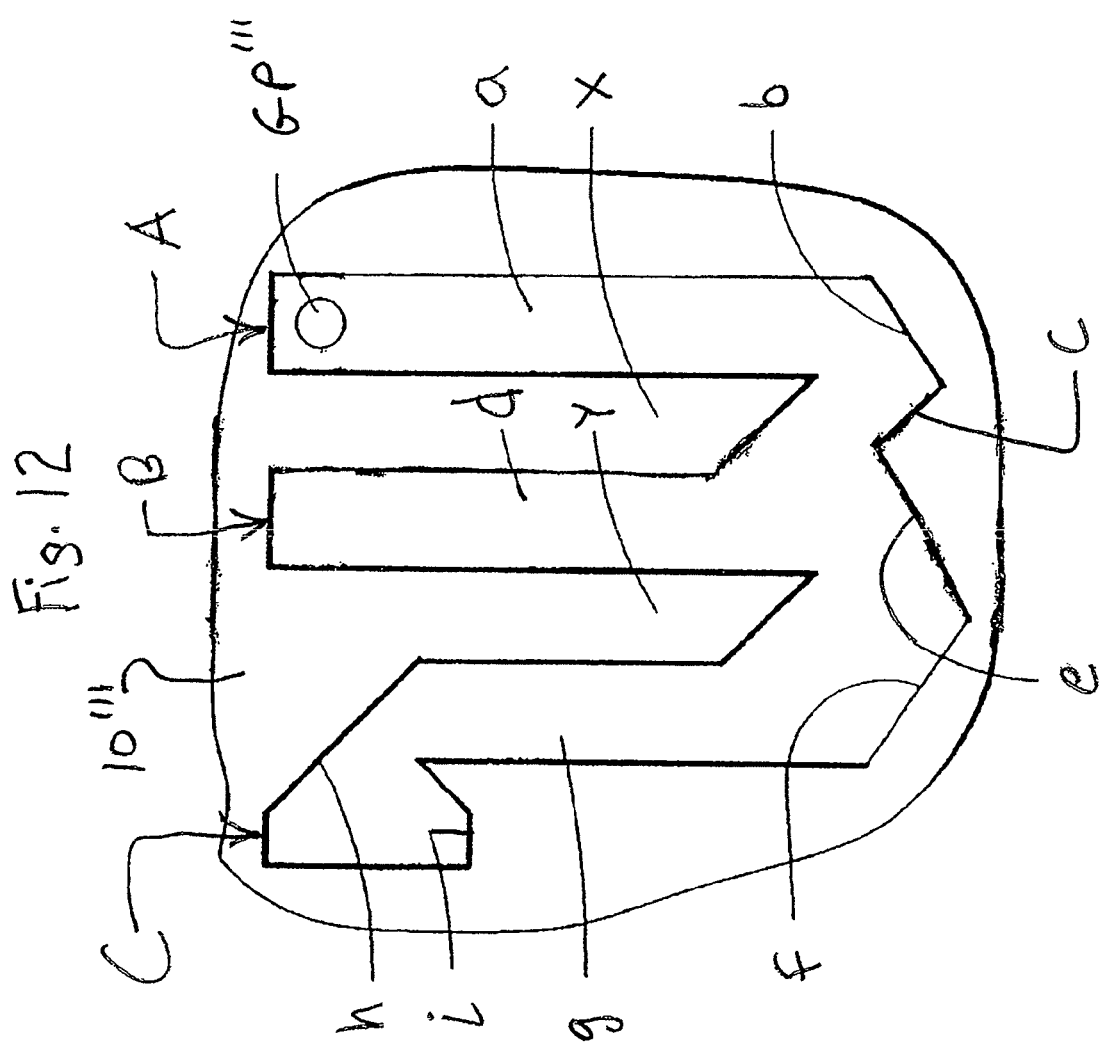
FIG. 12 shows a view of the body used in the needle assembly of FIG. 11 and shows the relative position of the guiding projection in the generally W-shaped guiding groove arrangement when the shield is in the position shown in FIG. 11.
Figure 13:
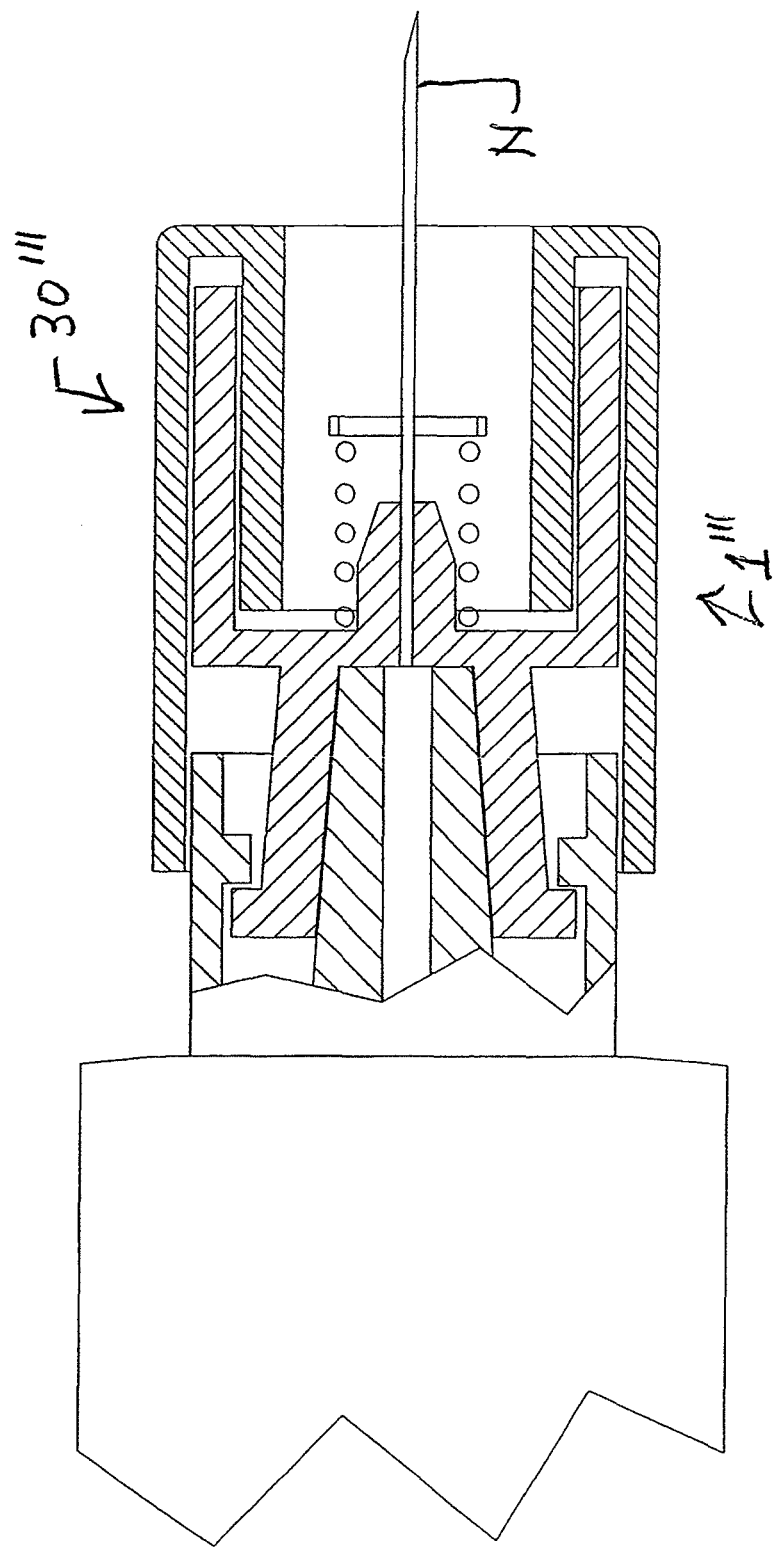
FIG. 13 shows a side cross-section view of needle assembly of FIG. 11 when the shield is in a first retracted position.
Figure 14:
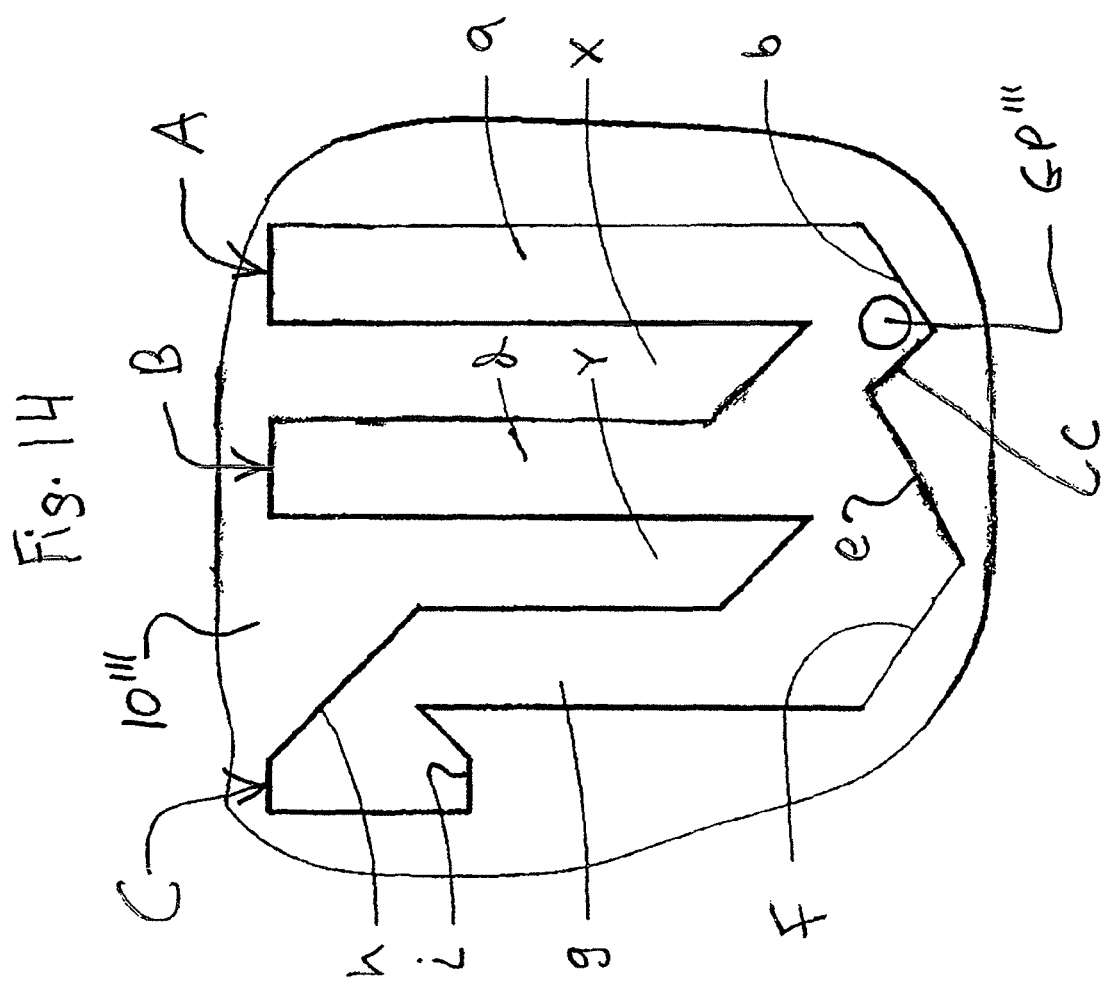
FIG. 14 shows a view of the body used in the needle assembly of FIG. 11 and shows the relative position of the guiding projection in the generally W-shaped guiding groove arrangement when the shield is in the position shown in FIG. 13.
Figure 15:
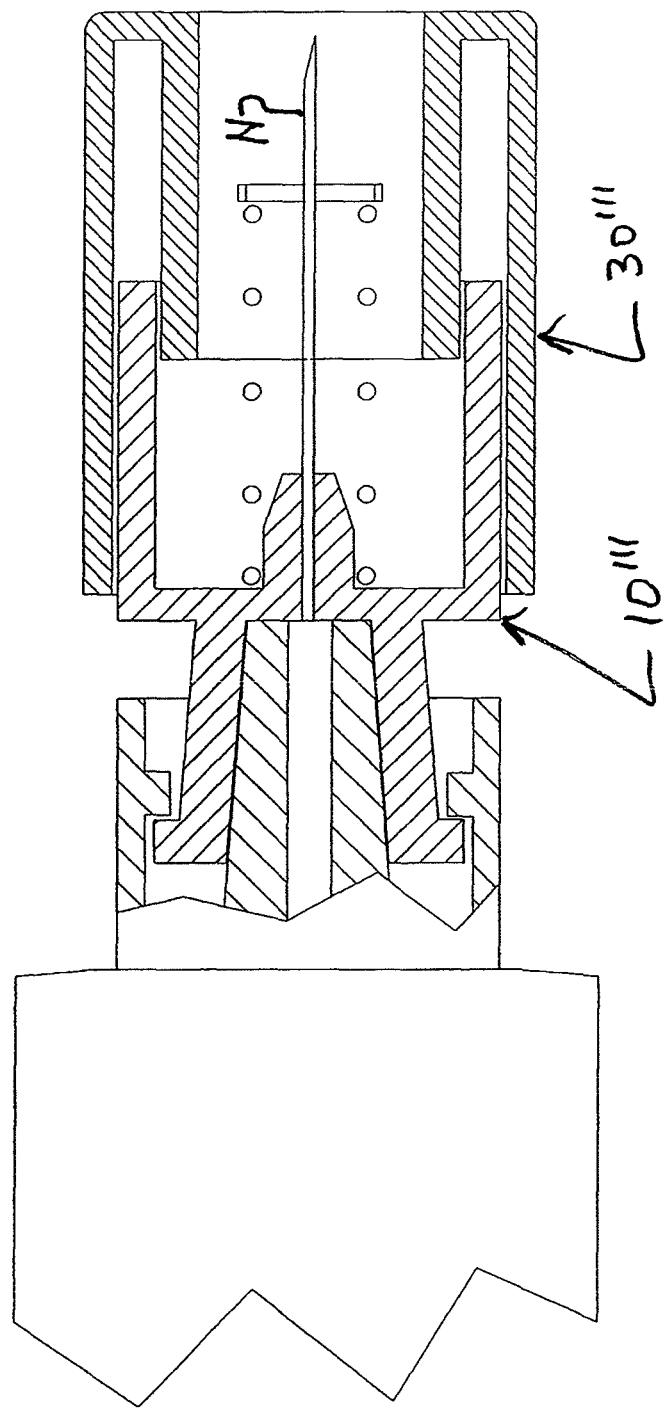
FIG. 15 shows a side cross-section view of needle assembly of FIG. 11 when the shield is in a second extended or needle covering position.
Figure 16:
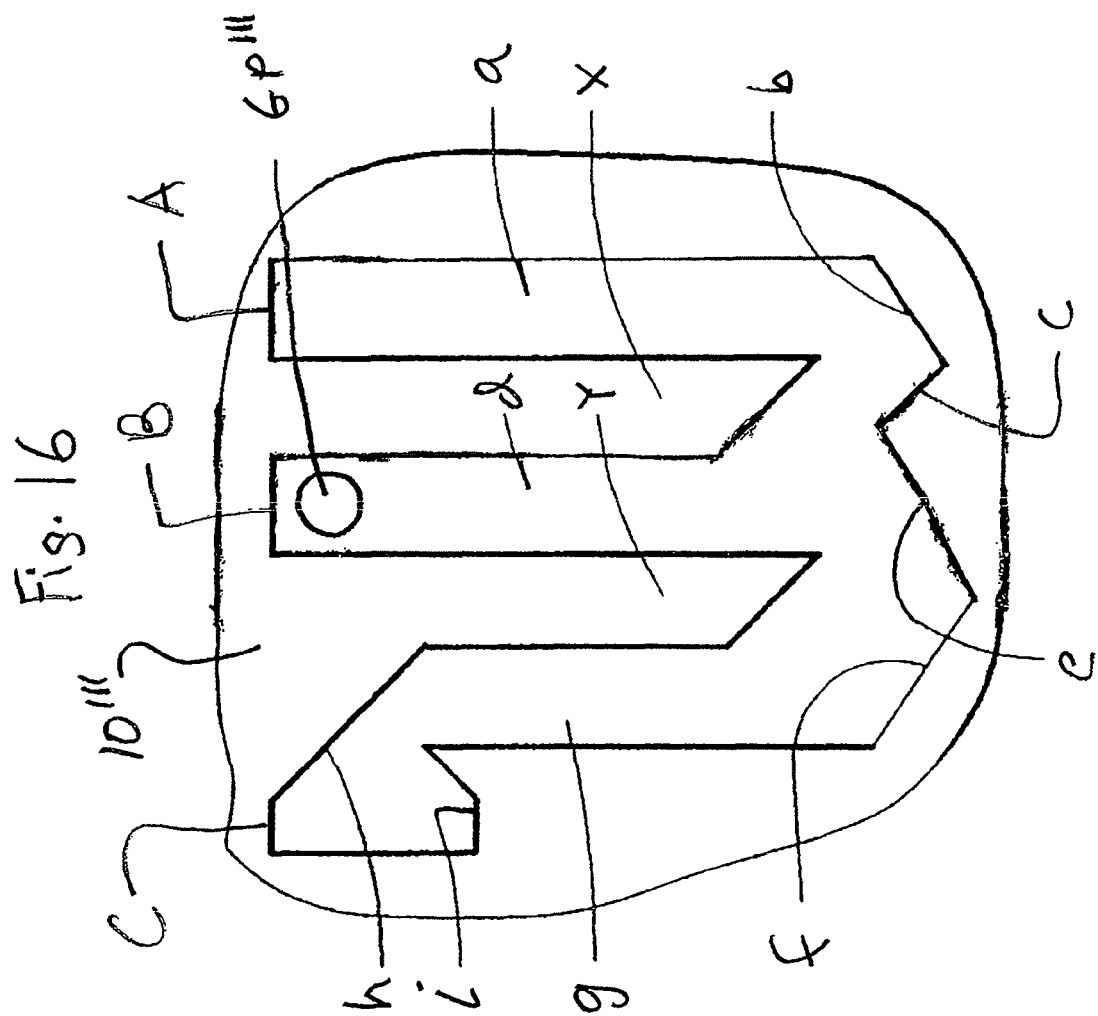
FIG. 16 shows a view of the body used in the needle assembly of FIG. 11 and shows the relative position of the guiding projection in the generally W-shaped guiding groove arrangement when the shield is in the position shown in FIG. 15.
Figure 17:
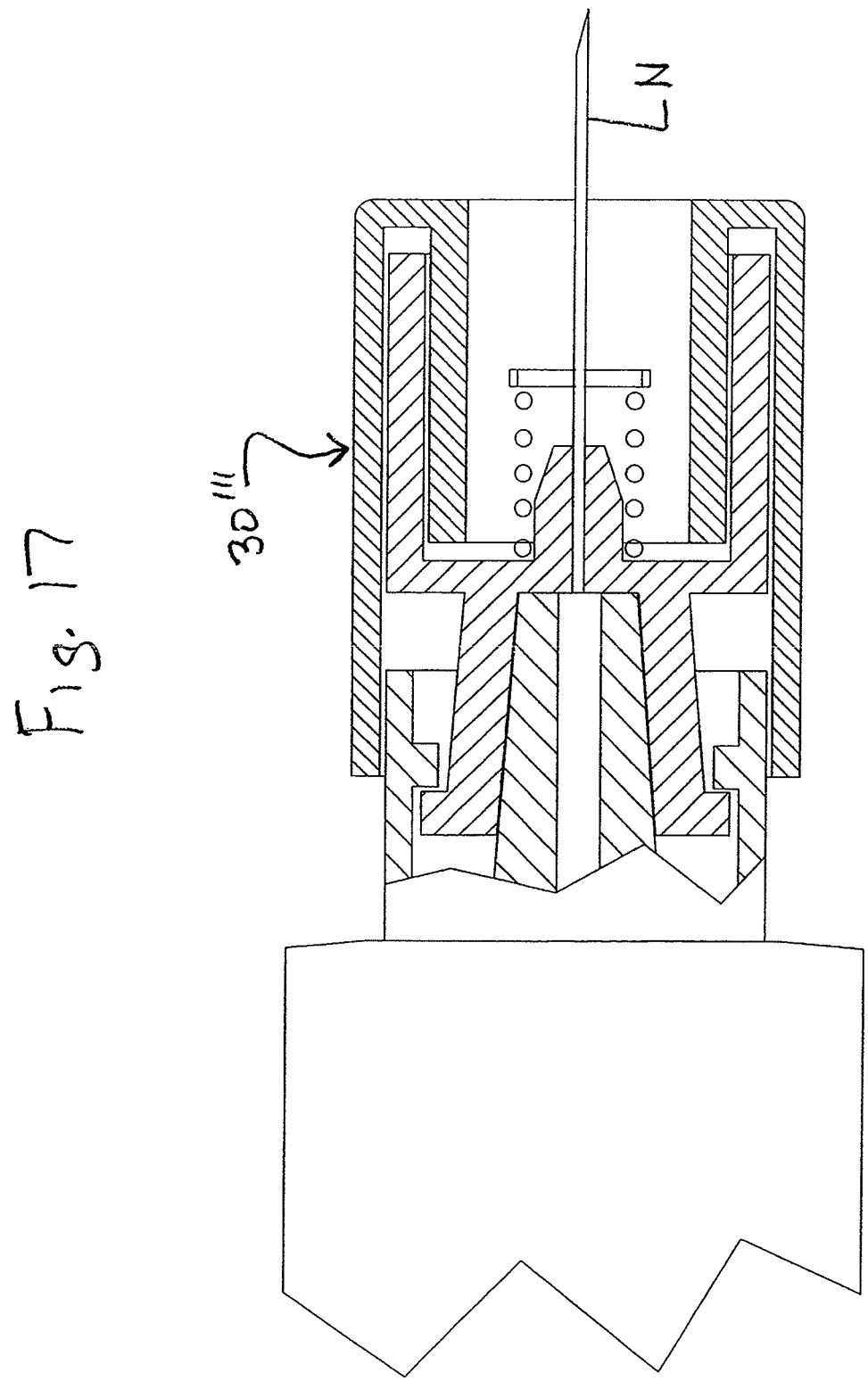
FIG. 17 shows a side cross-section view of needle assembly of FIG. 11 when the shield is in a second retracted position.
Figure 18:
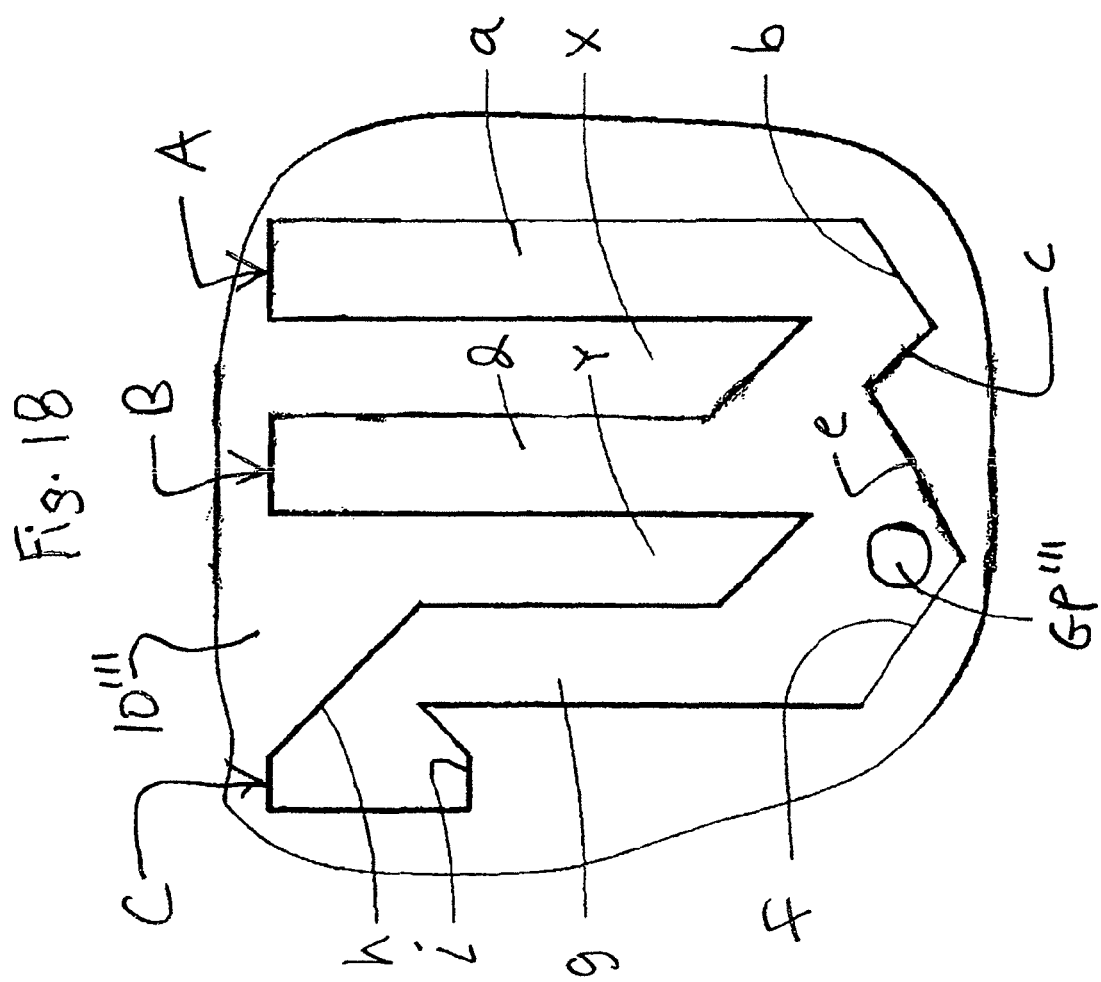
FIG. 18 shows a view of the body used in the needle assembly of FIG. 11 and shows the relative position of the guiding projection in the generally W-shaped guiding groove arrangement when the shield is in the position shown in FIG. 17.
Figure 19:
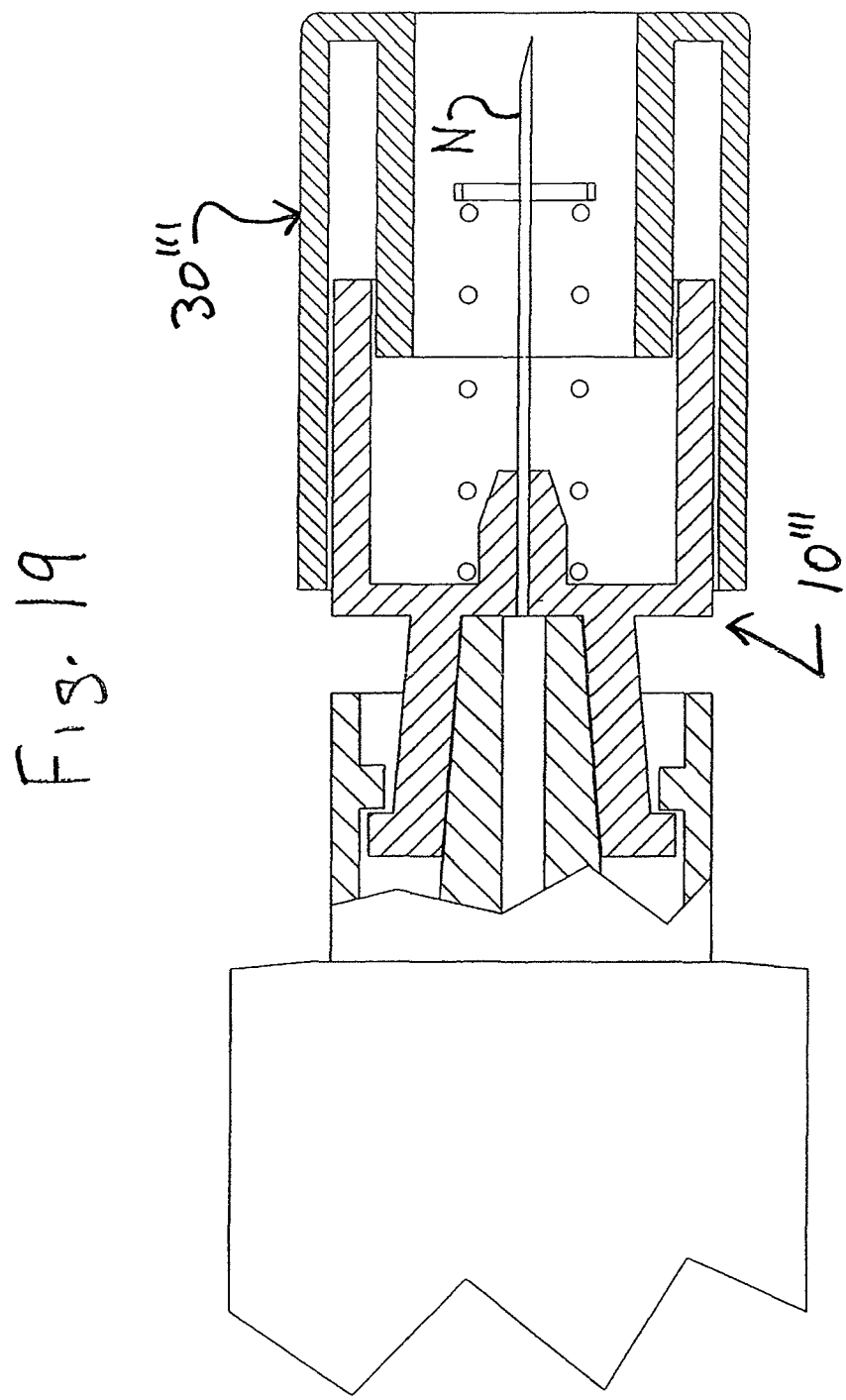
FIG. 19 shows a side cross-section view of needle assembly of FIG. 11 when the shield is in a third extended or needle covering position.

FIGS. 11-22 show a needle assembly 1''' in accordance with another embodiment of the invention. The assembly 1''' includes a body 10''', a needle N, a needle shield 30''' and a spring 50'''. In FIG. 11, the needle assembly 1''' is shown in an initial, intermediate, or prior-use configuration. In FIGS. 13 and 17, the needle assembly 1''' is shown in injection positions. FIGS. 15 and 19 show the shield 30''' is extended covering positions. Although not shown, a packaging needle cover (similar to that shown in FIG. 26) can be removably mounted to the same.

Figure 20:
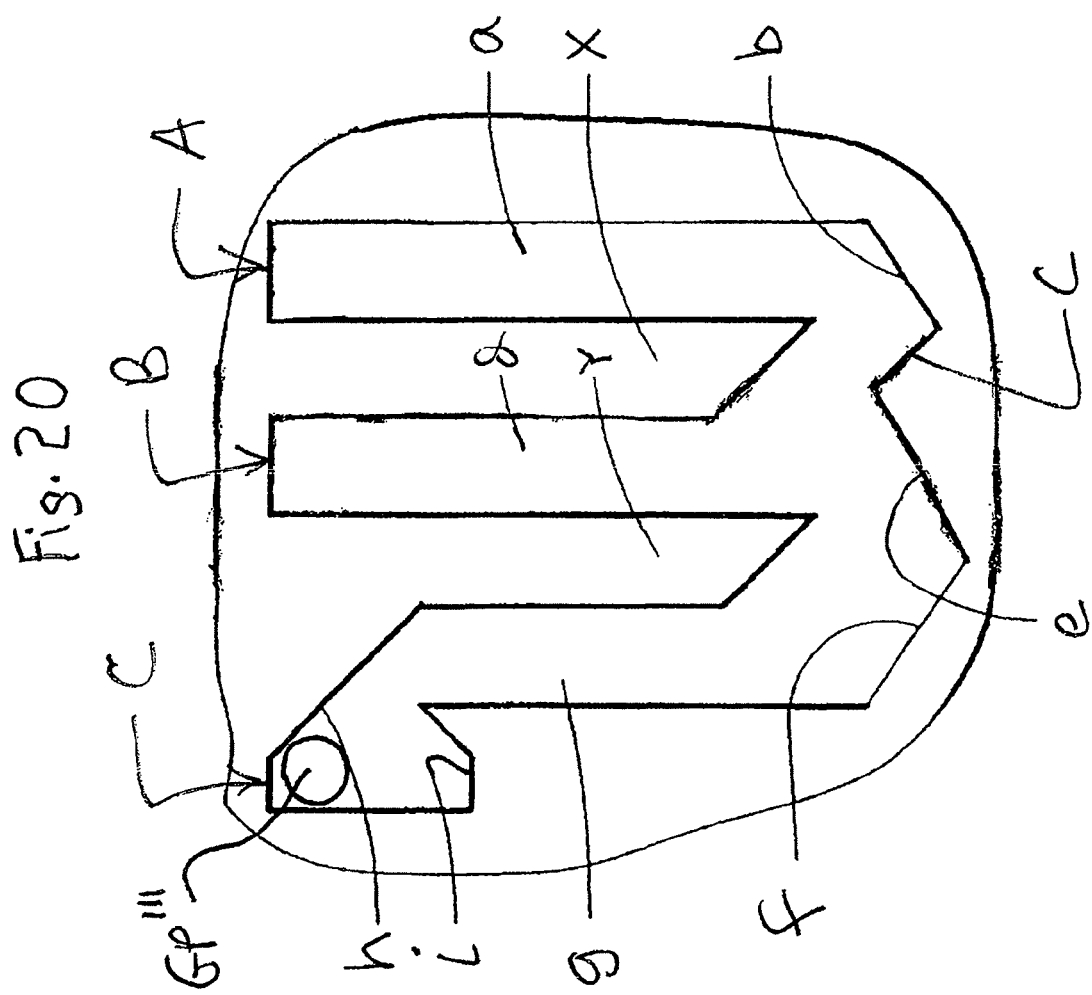
FIG. 20 shows a view of the body used in the needle assembly of FIG. 11 and shows the relative position of the guiding projection in the generally W-shaped guiding groove arrangement when the shield is in the position shown in FIG. 19.
Figure 21:
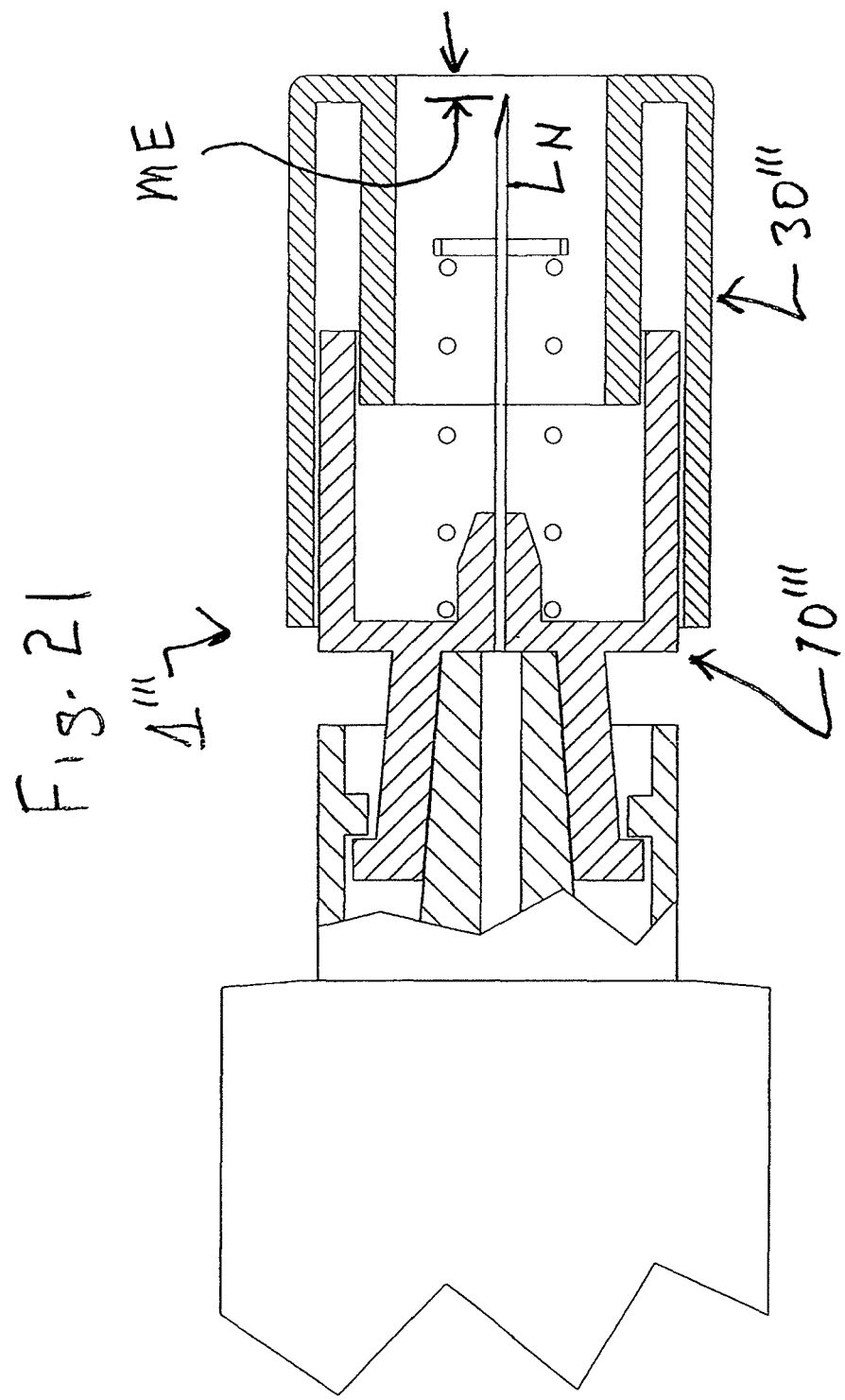
FIG. 21 shows the needle assembly of FIG. 19 and illustrates how the shield can move back slightly when in the locked needle covering position.
Figure 22:
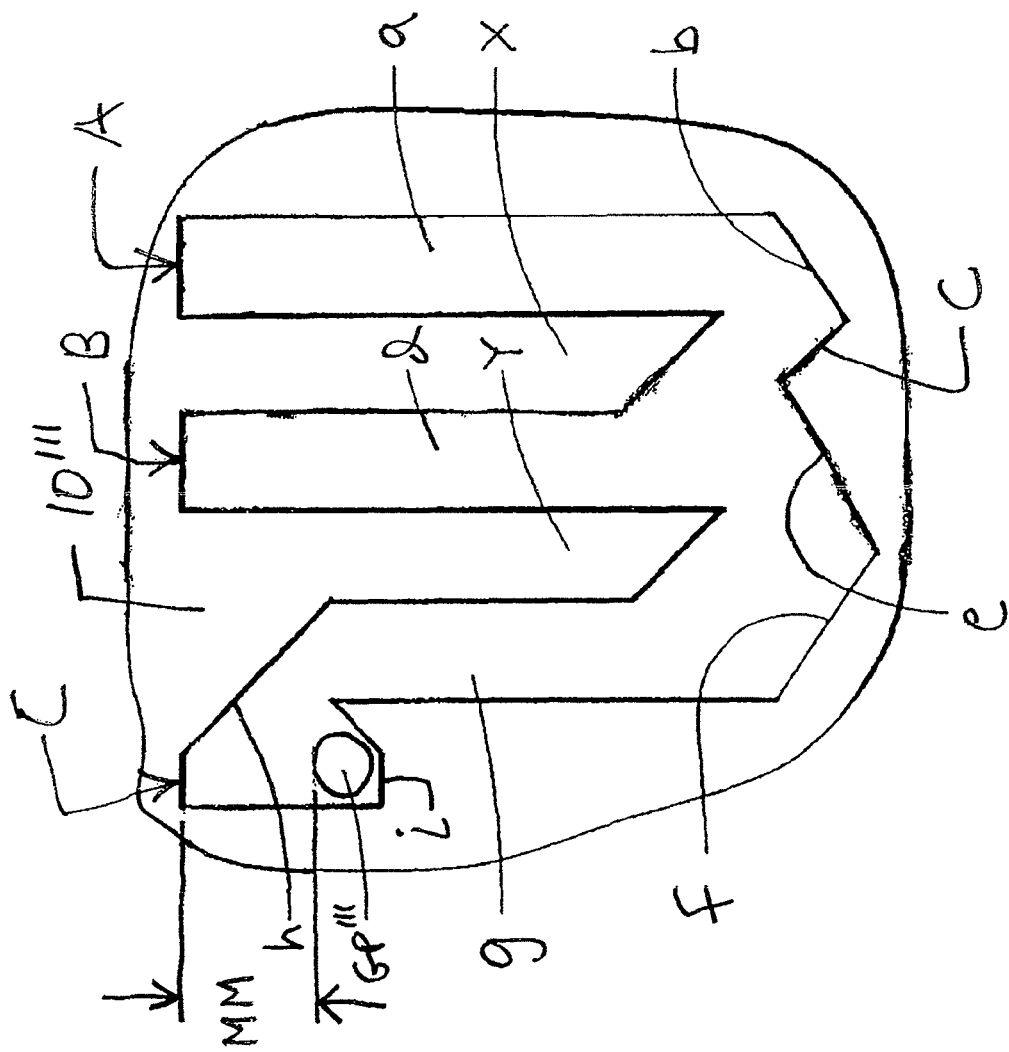
FIG. 22 shows a view of the body used in the needle assembly of FIG. 19 and shows the relative position of the guiding projection in the generally W-shaped guiding groove arrangement when the shield is in the position shown in FIG. 21.

The device shown in FIGS. 11-22 can function as follows. After the assembly 1''' is installed on the injection device S as shown in FIG. 11, a first mode includes moving the safety shield 30''' from the position shown in FIGS. 11 and 12 to a first retracted position during injection of the piercing portion of needle N into a surface shown in FIGS. 13 and 14, e.g., into a container containing a substance that can be suctioned into the injection device. When this happens, the guiding projection GP''' moves from position A in guide recess portion "a" as shown in FIG. 12 of a complex cam guiding recess arrangement until it contacts bottom surfaces "b" and "c". Due to the offset nature of the cam arrangement, once the spring 50″ causes the needle shield 30‴ to move axially in the proximal direction, the projection GB′″ shown in FIG. 14 will be guided into recess portion "d" (leftward and upward in FIG. 14) by the surface "c" and the angled surface at the bottom of island portion X. Once it enters portion "d" and reaches position B as shown in FIGS. 15 and 16. Another mode results when the safety shield 30‴ is caused to move to a second injection position as shown in FIGS. 17 and 18. When this happens, the guiding projection GP‴ moves from position B in guide recess portion "d" as shown in FIG. 16 of the complex cam guiding recess arrangement until it contacts bottom surfaces "e" and "f". Due to the offset nature of the cam arrangement, once the spring 50′ causes the needle shield 30′ to move axially in the proximal direction, the projection GB‴ shown in FIG. 18 will be guided into recess portion "g" (leftward and upward in FIG. 18) by the surface "f" and the angled surface at the bottom of island portion Y. Upon approaching angled surface "h", the projection GP′ is guided thereby leftward until it reaches position C as shown in FIG. 20. Due to the offset nature of the cam arrangement, once the spring 50‴ causes the needle shield 30‴ to again move axially in the proximal direction until it reaches position C, the projection GB′ shown in FIG. 20 will be axially confined between position "C" and surface "i". The space between these surfaces is such that the needle shield 30′ can move, at most, the slight axial amount MM, but that is sufficient to maintain at least a desirable spacing as shown in FIGS. 21 and 22, and designated with the dimension ME. In the position shown in FIGS. 19-22, the needle shield 30‴ is effectively locked in the fully extended position such that the user is prevented from reusing the device 1‴ and can safely discard the same.

Figure 23:
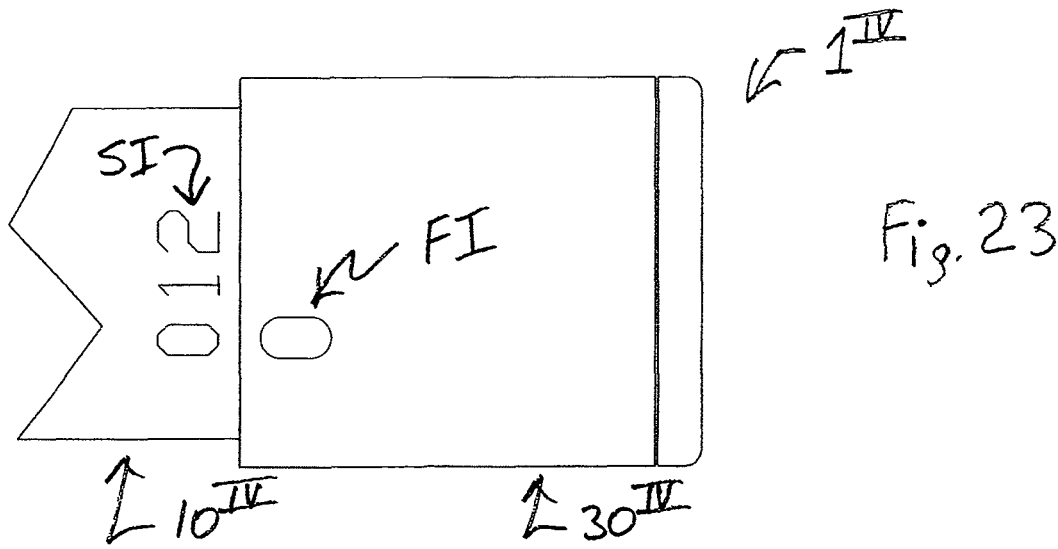
FIG. 23 shows a side view of needle assembly similar to that of FIG. 11 but utilizing a visual and/or tactile indication system. In the position shown in FIG. 23, a recess or projection arranged on the shield is shown in the position indicated by the number "0" on the body. This is characteristic of the initial shield position shown in FIGS. 11 and 12.
Figure 24:
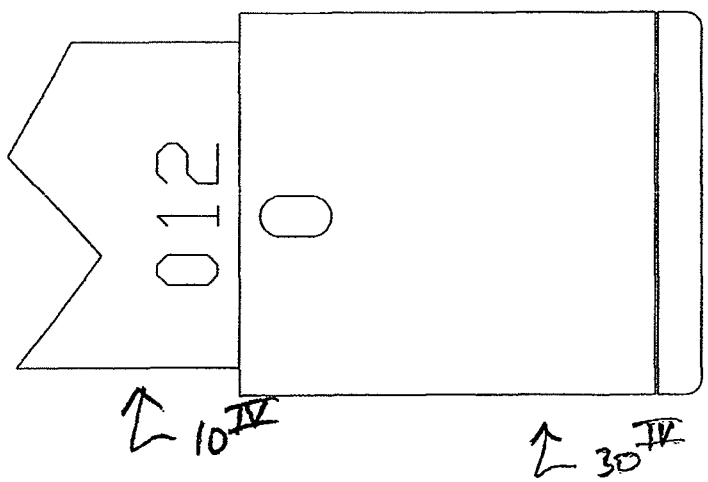
FIG. 24 shows the needle assembly of FIG. 23 with the shield in another rotational position. In the position shown in FIG. 24, a recess or projection arranged on the shield is shown in the rotational position indicated by the number "1" on the body. This is characteristic of the second extended shield position shown in FIGS. 15 and 16.
Figure 25:
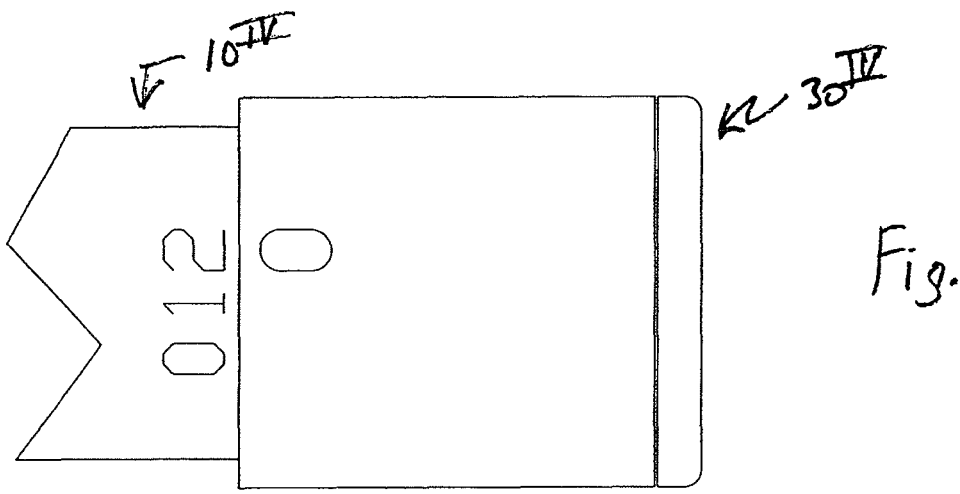
FIG. 25 shows the needle assembly of FIG. 23 with the shield in yet another rotational position. In the position shown in FIG. 25, a recess or projection arranged on the shield is shown in the rotational position indicated by the number "2" on the body. This is characteristic of the third extended shield position shown in FIGS. 19 and 20.

FIGS. 23-25 shows a needle assembly similar to that of FIG. 11 but utilizing a visual and/or tactile indication system. Like previous embodiments, the assembly $1^{IV}$ includes a body $10^{IV}$ and a needle shield $30^{IV}$. This system includes first indicia or an indicator FI and a second indicia or indicator SI and provides information to the user of the rotational position of the needle shield $30^{IV}$ in relation to the body $10^{IV}$. In the position shown in FIG. 23, the indicia FI can have the form of a recess or projection arranged on the shield $30^{IV}$ and is shown in the position indicated by the number "0" on the body. This is characteristic of or corresponds to the initial shield position A shown in FIGS. 11 and 12. FIG. 24 shows the needle assembly of FIG. 23 with the shield $30^{IV}$ in another rotational and fully extended position. In the position shown in FIG. 24, the recess or projection FI arranged on the shield $30^{IV}$ is shown in the rotational position indicated by the number "1" on the body $10^{IV}$. This is characteristic of or corresponds to the second extended shield position B shown in FIGS. 15 and 16. FIG. 25 shows the needle assembly of FIG. 23 with the shield $30^{IV}$ in yet another rotational position, i.e., a final locked extended position. In the position shown in FIG. 25, the recess or projection FI arranged on the shield $30^{IV}$ is shown in the rotational position indicated by the number "2" on the body $10^{IV}$. This is characteristic of the third or final extended shield position C shown in FIGS. 19 and 20.

Figure 26:
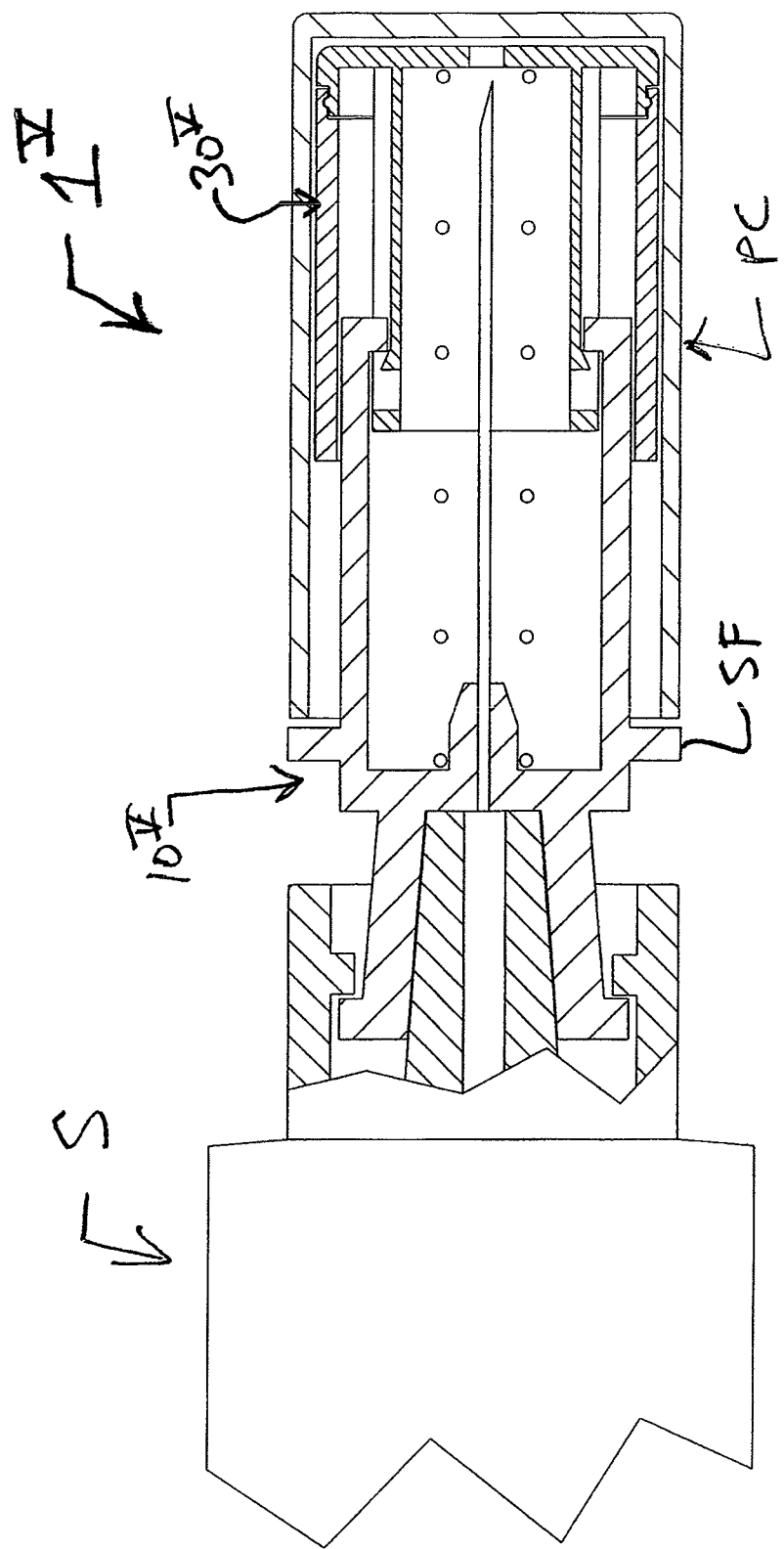
FIG. 26 shows a side cross-section view of a needle assembly mounted to the syringe of FIG. 1 in accordance with another non-limiting embodiment of the invention. The shield of needle assembly is shown in an initial, intermediate, or prior-use configuration. A packaging and/or protective needle cover is shown installed on the needle assembly which will be removed at the point of use and which prevents movement of the needle shield.
Figure 27:
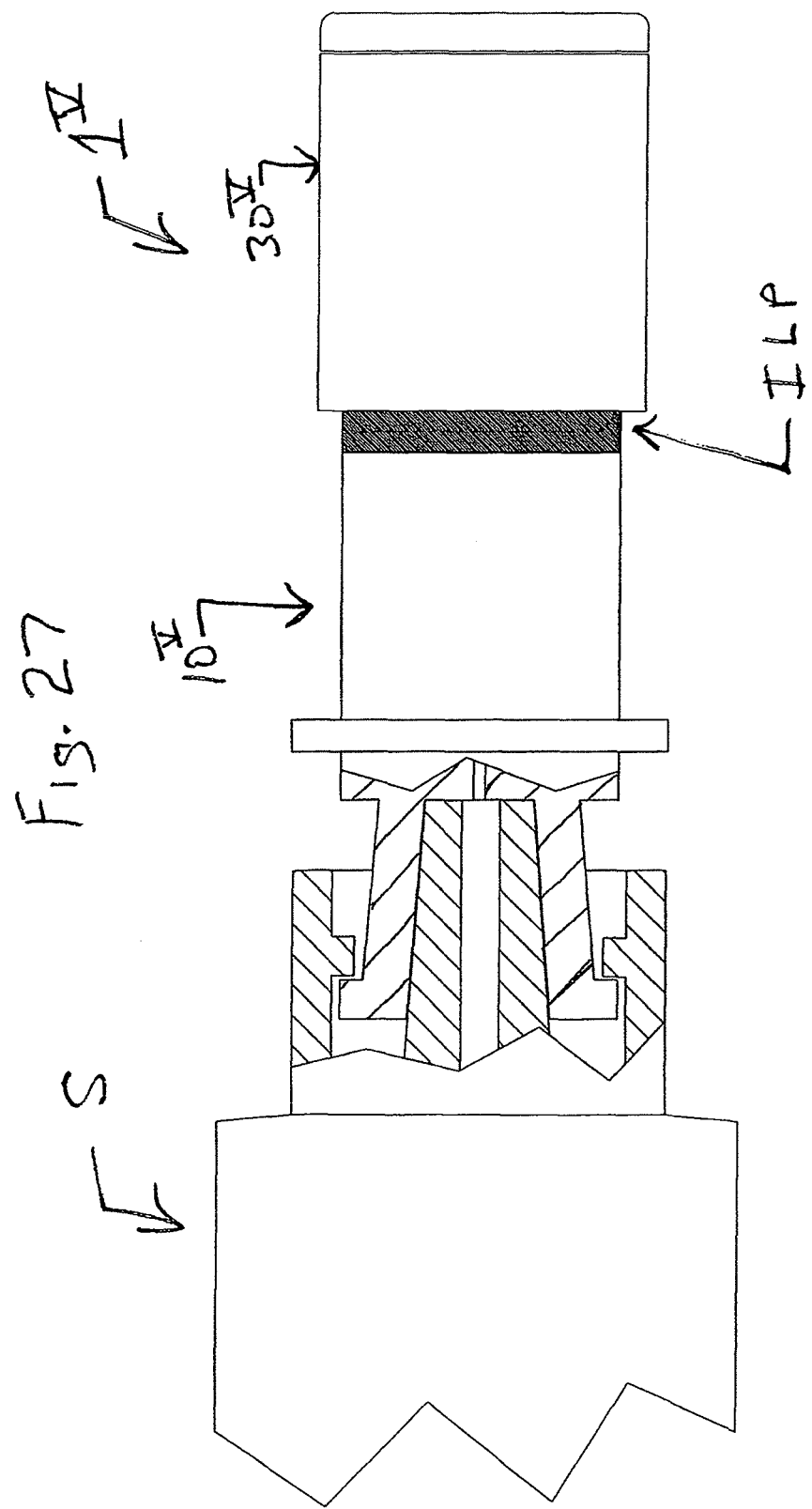
FIG. 27 shows the needle assembly of FIG. 26 with the shield in the locked post-use position and with an indicator of the locked position being visible. This indicator can be a visual indicator band, e.g., a red band, or a tactile band, e.g., a rough or knurled band. The band is no visible when the shield is in the initial position.

FIGS. 26 and 27 show a needle assembly $1^V$ mounted to the syringe S of FIG. 1 in accordance with another non-limiting embodiment of the invention. Like previous embodiments, the assembly $1^V$ includes a body $10^V$ and a needle shield $30^V$. The shield $30^V$ of needle assembly is shown in an initial, intermediate, or prior-use configuration. A packaging and/or protective needle cover PC is shown installed on the needle assembly which can be removed at the point of use and which prevents movement of the needle shield. Furthermore, in this embodiment, the body $10^V$ includes an external shoulder or flange SF which can function as a distal (and or secondary) stop for shield $30^V$ and also as a stop for the protective cover PC. The cover PC can function to prevent or minimize the chance of axial movement of the needle shield $30^V$ relative to the body $10^V$. Additionally, this embodiment utilizes a visual indicator ILP in the form of a ring-shaped band. FIG. 27 shows the needle assembly of FIG. 26 with the shield $30^V$ in the locked post-use position in and with an indicator ILP of the locked position being visible. This indicator ILP can be a visual indicator band, e.g., a red band, or a tactile band, e.g., a rough or knurled band. The band is not visible when the shield $30^V$ is in the initial position shown in FIG. 26. One can implement such a system on any of the herein disclosed embodiment if desired. In an optional embodiment, the cover PC can also be threaded or otherwise removably coupled to the body or the shoulder SF which would prevent the user from accidentally removing the cover PC.

Figure 28:
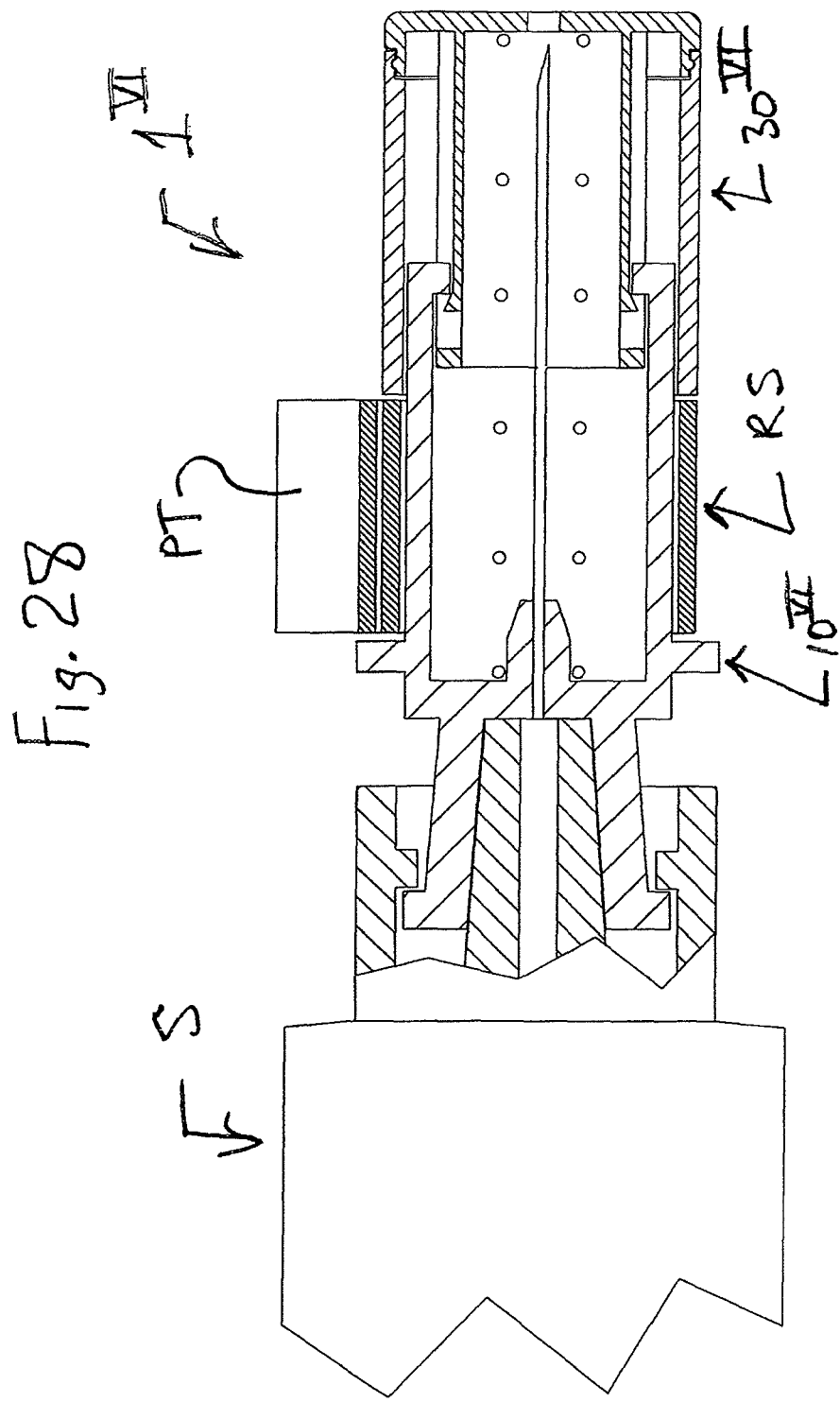
FIG. 28 shows a side cross-section view of a needle assembly mounted to the syringe of FIG. 1 in accordance with another non-limiting embodiment of the invention. The shield of needle assembly is shown in an initial, intermediate, or prior-use configuration. A packaging and/or protective removable strip is shown wound onto or installed on the needle assembly which will be removed by peeling off (upon griping the pull tab) at the point of use and which prevents movement of the needle shield.

FIG. 28 shows a needle assembly $1^{VI}$ mounted to the syringe S of FIG. 1 in accordance with another non-limiting embodiment of the invention. Like previous embodiments, the assembly $1^{VI}$ includes a body $10^{VI}$, a spring and a needle shield $30^{VI}$. The shield $30^{VI}$ of needle assembly $1^{VI}$ is shown in an initial, intermediate, or prior-use configuration. A packaging and/or protective removable strip PT is shown installed onto the needle assembly $1^{VI}$ which will be removed by, e.g., peeling off (upon griping the pull tab) at the point of use and which prevents movement of the needle shield $30^{VI}$. Until the band PT is removed, it serves, among other things, to provide the use a visual indicator that the product has not yet been used and prevents intentional or accidental distal axial movement of the needle shield $30^{VI}$ relative to the body $10^{VI}$.

Figure 29:
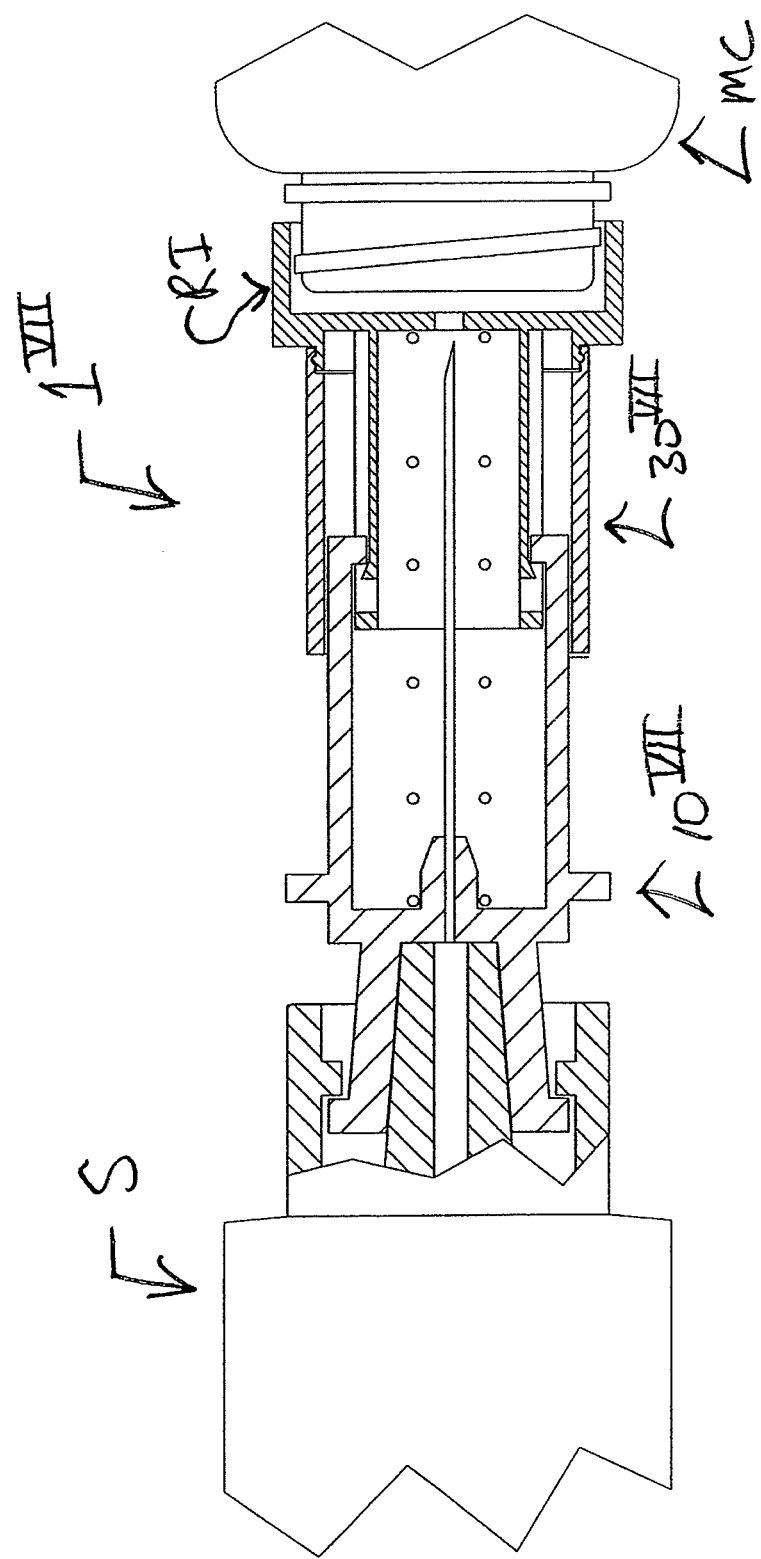
FIG. 29 shows a side cross-section view of a needle assembly mounted to the syringe of FIG. 1 in accordance with another non-limiting embodiment of the invention. The shield of needle assembly is shown in an initial, intermediate, or prior-use configuration. A proximal end of the shield has a receiving interface which makes it easier to align the needle assembly with the neck of a medicine container. Once in the position shown in FIG. 29, the user can move the syringe toward the medicine container and then withdraw fluid into the syringe via the needle.

FIG. 29 shows a needle assembly $1^{VII}$ mounted to the syringe S of FIG. 1 in accordance with another non-limiting embodiment of the invention. Like previous embodiments, the assembly $1^{VII}$ includes a body $10^{VII}$, a spring and a needle shield $30^{VII}$. The shield $30^{VII}$ of needle assembly $1^{VII}$ is shown in an initial, intermediate, or prior-use configuration. A proximal end of the shield $30^{VII}$ has a receiving interface RI which makes it easier to align the needle assembly $1^{VII}$ with the neck of a medicine container MC. Once in the position shown in FIG. 29, the user can move the syringe S toward the medicine container MC in order to cause the needle to enter into the container MC and then withdraw the substance or fluid into the syringe S via the needle.

Figure 30:
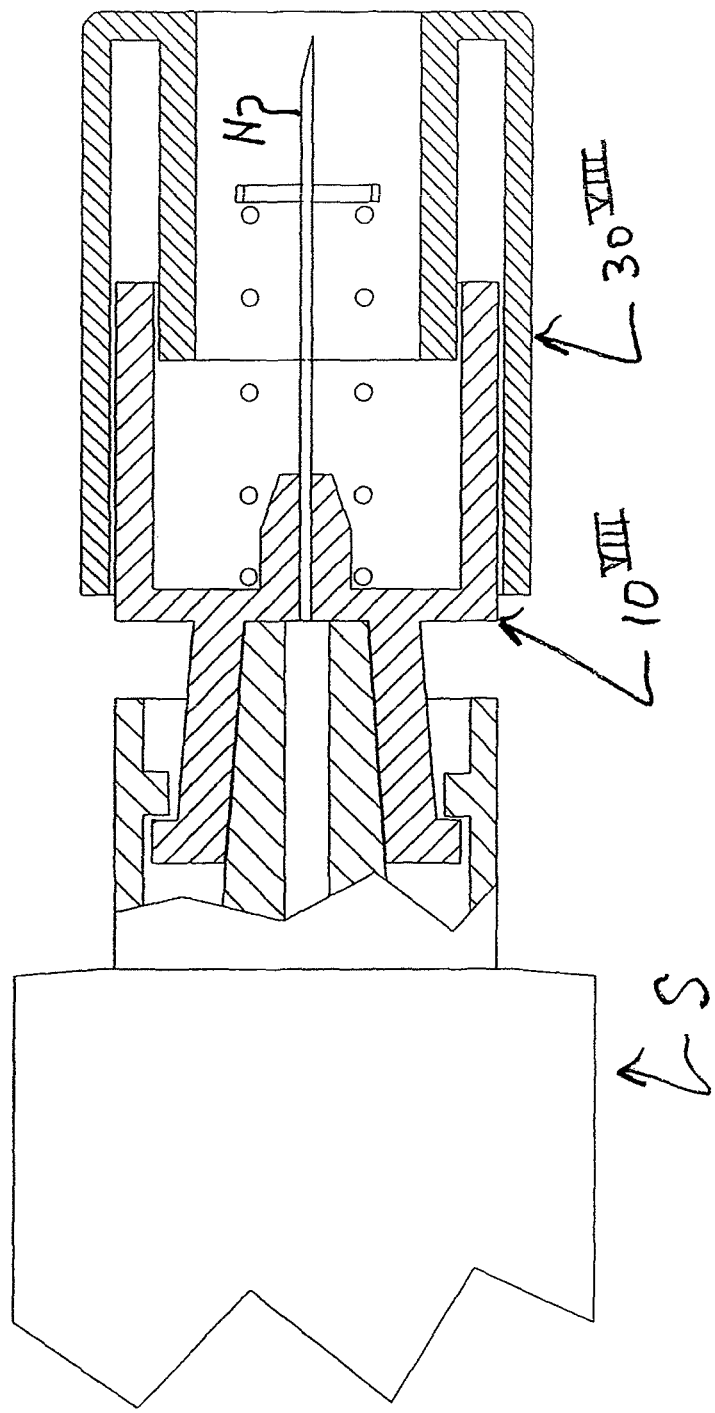
FIG. 30 shows a side cross-section view of needle assembly similar to that of FIG. 11 but utilizing a different cam-guiding system.
Figure 31:
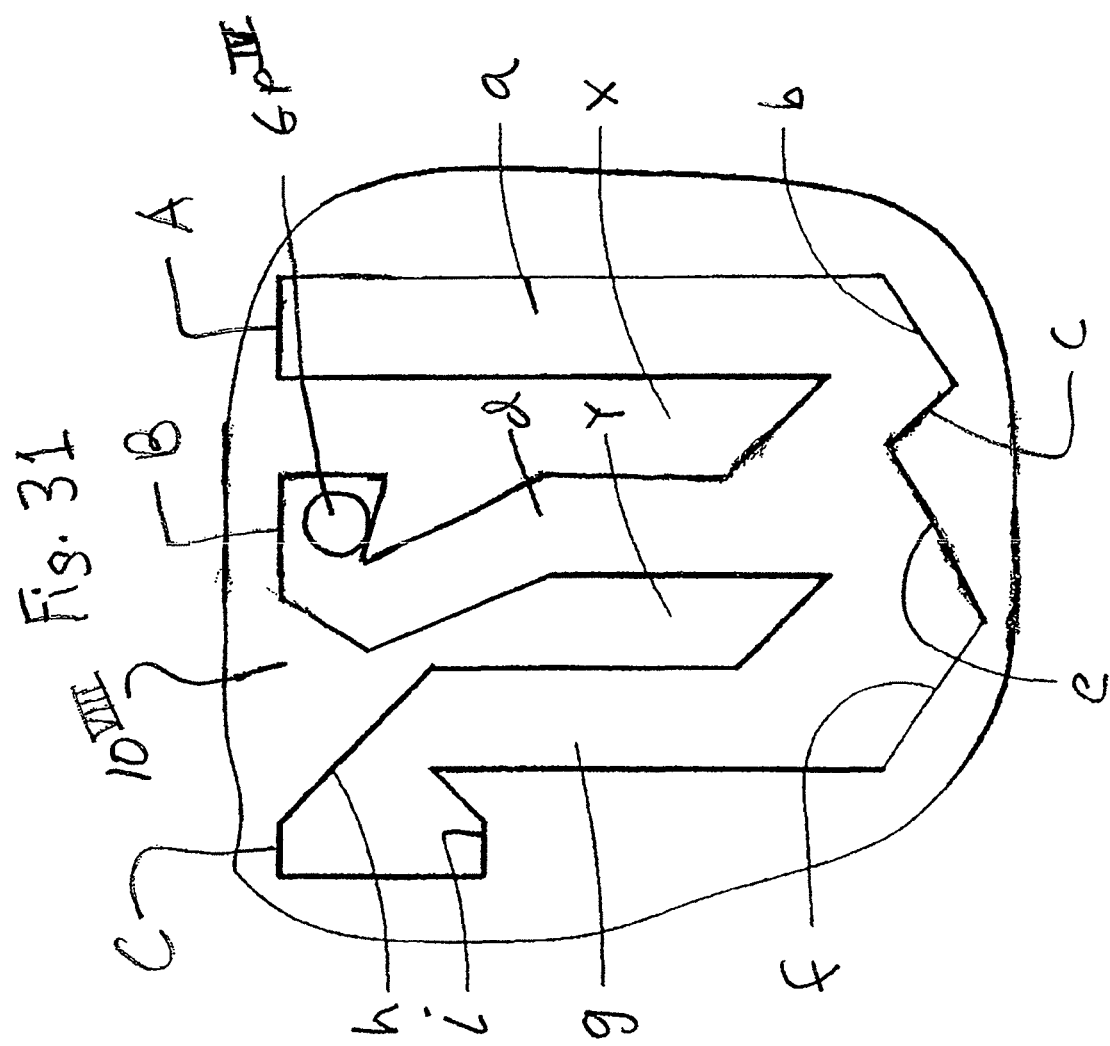
FIG. 31 shows a view of the body used in the needle assembly of FIG. 30 and shows the relative position of the guiding projection in the generally W-shaped guiding groove arrangement when the shield is in the position shown in FIG. 30. In the position shown in FIG. 31, the safety shield is prevent from moving axially back until a user manually or selectively rotates the shield at least partially so that the guidable projection can move back along the middle guide track.

FIGS. 30 and 31 shows a needle assembly $1^{VIII}$ which can be similar to that of FIG. 11 but which can utilize a different cam-guiding system. In FIGS. 30 and 31, the shield $30^{VIII}$ is shown in a second extended or needle covering position relative to the body $10^{VIII}$. The position of the guiding projection $GP^{IV}$ in the generally W-shaped guiding groove arrangement of the body $10^{VIII}$ when the shield $30^{VIII}$ is in the position shown in FIG. 30 is that shown in FIG. 31. In the position shown in FIG. 31, the safety shield $30^{VIII}$ is prevent from moving axially back (and/or is releasably retained in position B) until a user manually or selectively rotates the shield $30^{VIII}$ at least partially so that the guidable projection $GP^{IV}$ can move back along the middle guide track "d". The assembly $1^{VIII}$ otherwise functions in a manner similar to the embodiment shown in FIG. 11.

In addition to the herein disclosed features, each herein disclosed needle assembly can also utilize one or more features disclosed in U.S. application 61/443,958 filed on Feb. 17, 2011 to SCHRAGA and/or U.S. application Ser.

No. 13/398,173 to SCHRAGA filed Feb. 16, 2012. The disclosure of each of these applications is hereby expressly incorporated by reference in its entirety. In accordance with at least one embodiment, the device of the instant application additionally includes an embodiment similar to FIG. 1 (or other figures such as e.g., FIG. 31) of U.S. 61/443,958 or U.S. Ser. No. 13/398,173 (but otherwise resembling FIG. 2 of the instant application) wherein the puncturing end of the needle projects past the skin contacting end of the needle shield when the device is in the original or pre-use position. This allows the user to see the needle end after a protective cap is removed and before the device is used. It should be understood that embodiments other than FIG. 2 can be so modified so that the needle end is visible and/or not covered by the needle shield when the device is in the pre-use or initial position.

Figure 32:
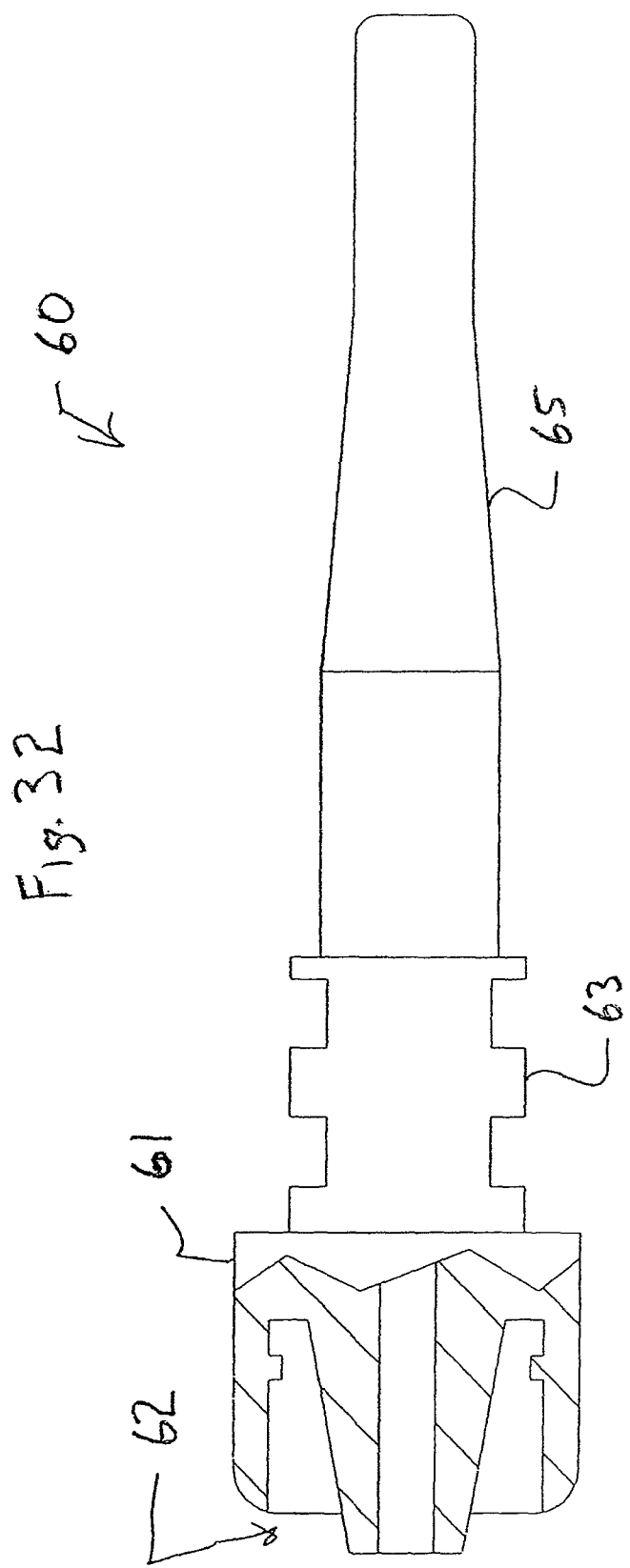
FIG. 32 shows a side partial cross-section view of a needle assembly interface for a fluid sampling device which can be utilized in accordance with another non-limiting embodiment of the invention. The interface includes a luer-lock interface connectable with the luer-lok interface of the needle assemblies disclosed herein.
Figure 33:
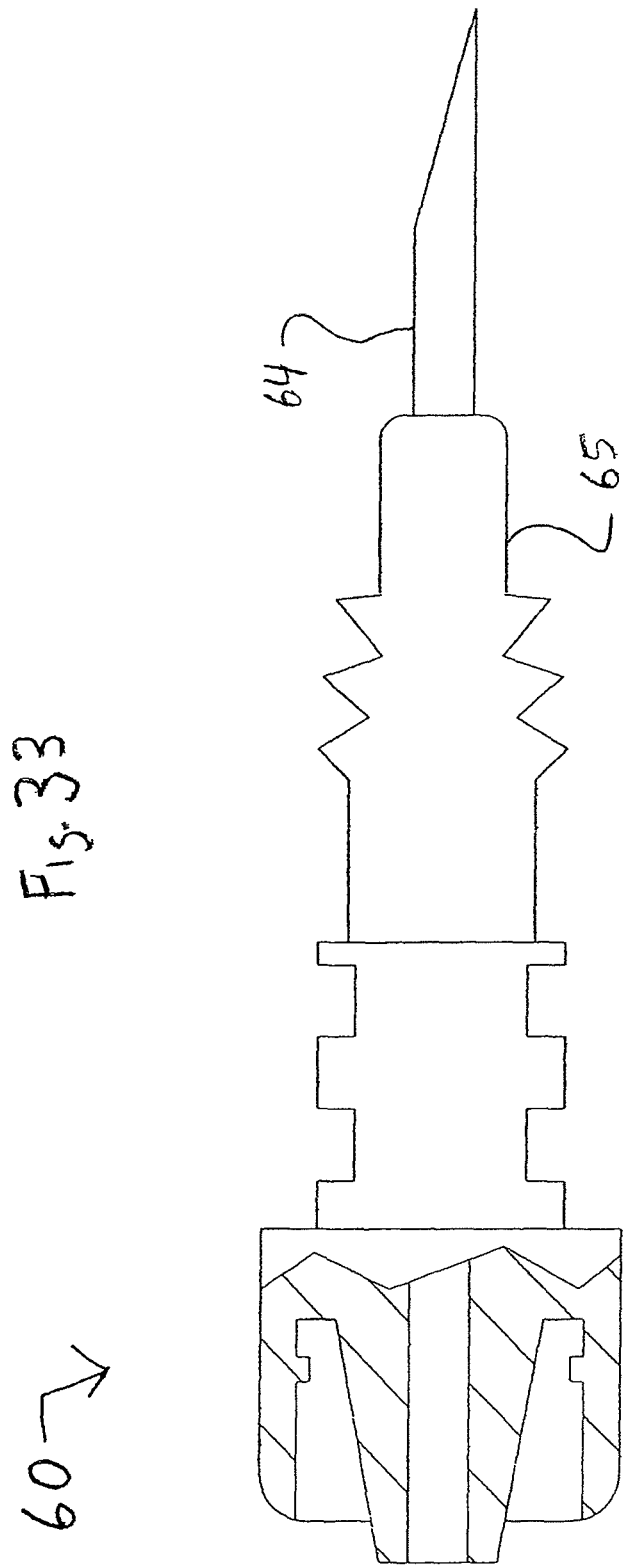
FIG. 33 shows the needle assembly interface of FIG. 32 with rear needle exposed. This occurs when the interface is installed on a fluid sampling device and a sample container in inserted therein.
Figure 34:
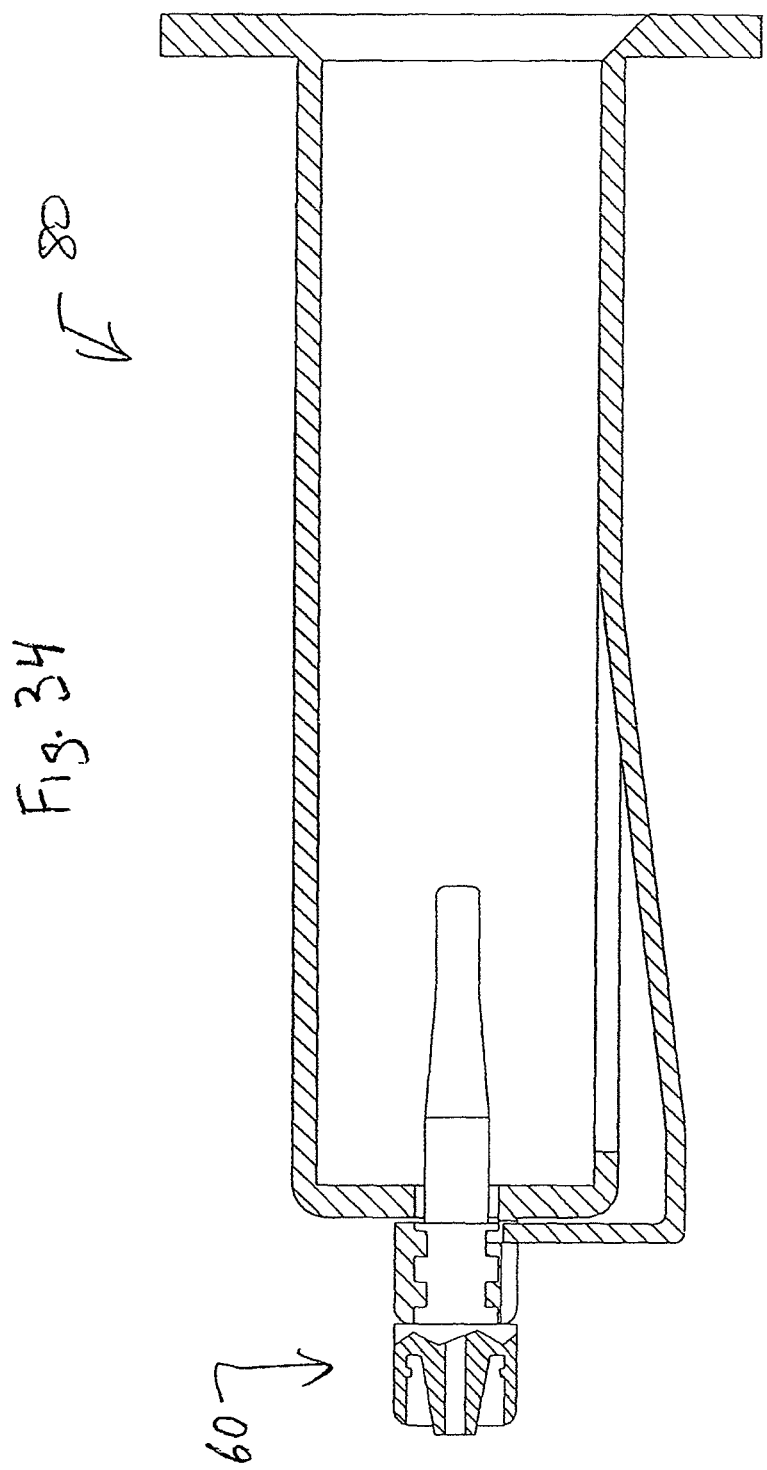
FIG. 34 shows the needle assembly interface of FIG. 32 installed on a fluid sampling device. While in the configuration shown in FIG. 34, a user can install any one of the needle assemblies shown in FIGS. 2-29 on the needle assembly interface in a manner similar to being installed on the syringe of FIG. 1.

FIGS. 32-34 shows a needle assembly interface 60 for a fluid sampling device 80 which can be utilized in accordance with another non-limiting embodiment of the invention. The interface 60 includes a luer-lock interface connectable with the luer-lok interface of any of the needle assemblies $1-1^{VIII}$ disclosed herein. The interface 60 includes a connecting interface end 61 having an interface 62 that can connect to a needle assembly discuss above. Portion 63 serves to axially retain and mount the unit 60 to the device 80 (see FIG. 34). A flexible and retractable cover member 65 covers an inner needle 64. Additional details of such fluid sampling devices are disclosed in among other documents, U.S. Application No. 61/480,787 filed Apr. 29, 2011 to SCHRAGA, U.S. application No. 61/498,133 filed Jun. 17, 2011 to SCHRAGA, and US 2010/0286558 published on Nov. 11, 2010. The disclosure of each of these applications is hereby expressly incorporated by reference in their entireties.

Figure 35:
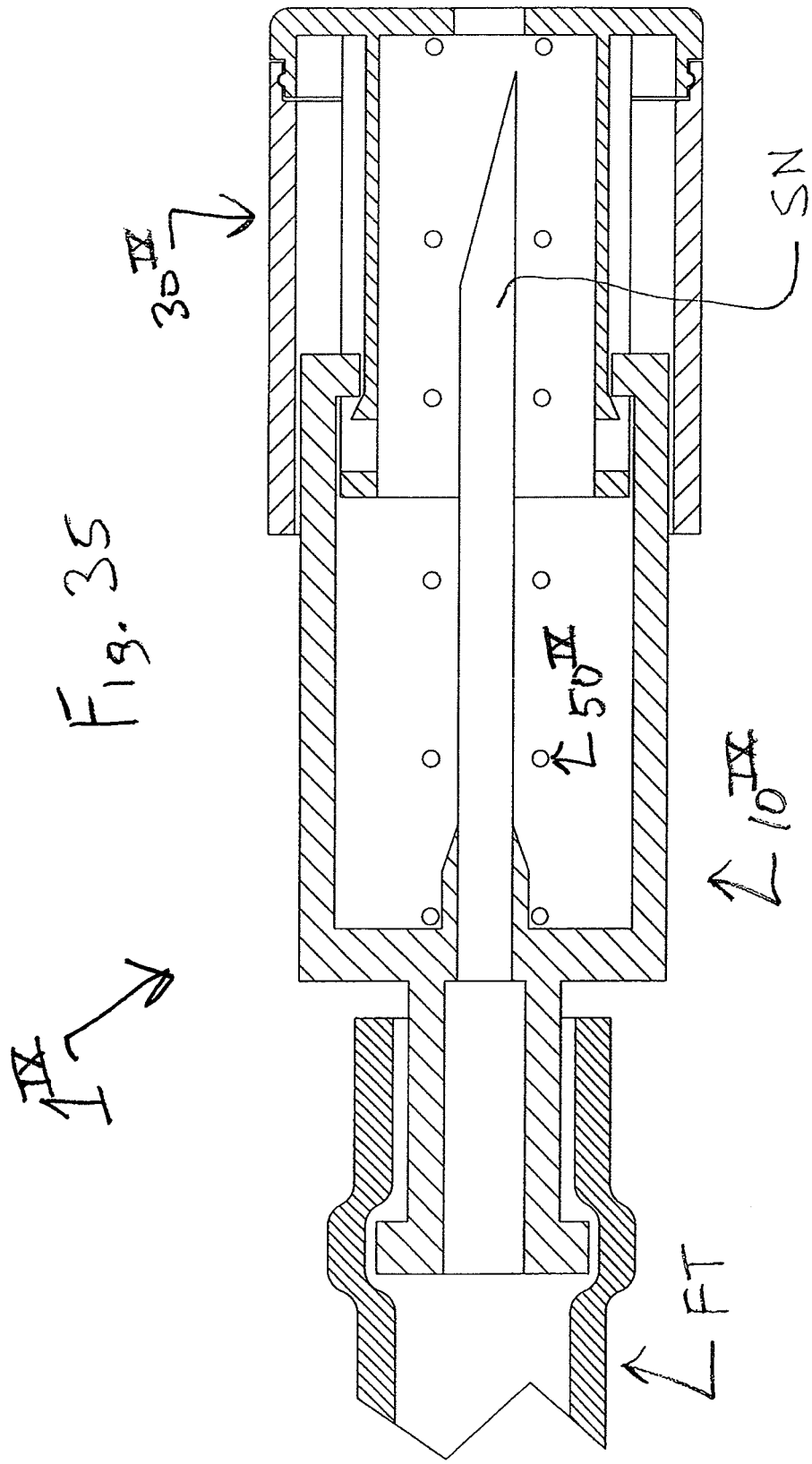
FIG. 35 shows a side cross-section view of a spike needle assembly mounted to an end of flexible tubing in accordance with another non-limiting embodiment of the invention. The shield of needle assembly is shown in an initial, intermediate, or prior-use configuration. A distal end of the needle assembly has a connecting interface which can be connected to an end of flexible tubing. Unlike the previous embodiments, the needle in this embodiment is a large gauge spike for use in IV applications and can puncture things such as medical bags and the like or other things typically punctured with a medical spike.

FIG. 35 shows a spike needle assembly $1^{IX}$ mounted to an end of flexible tubing FT in accordance with another non-limiting embodiment of the invention. The shield $30^{IX}$ of needle assembly $1^{IX}$ is shown in an initial, intermediate, or prior-use configuration and is biased via a spring $50^{IX}$. A distal end of the needle assembly $1^{IX}$ has a connecting interface which can be connected to an end of flexible tubing FT. Unlike the previous embodiments, the needle in this embodiment is a large gauge spike SN for use in IV applications and can puncture things such as medical bags and the like (or other things typically punctured with a medical spike). The assembly $1^{IX}$ can otherwise function is a manner similar to that of other herein disclosed needle assemblies.

The devices described herein can also utilize one or more features disclosed in the documents expressly incorporated by reference herein. Furthermore, one or more of the various parts of the device can preferably be made as one-piece structures by e.g., injection molding, when doing so reduces costs of manufacture. Non-limiting materials for most of the parts include synthetic resins such as those approved for syringes, blood collection devices, or other medical devices. Furthermore, the invention also contemplates that any or all disclosed features of one embodiment may be used on other disclosed embodiments, to the extent such modifications function for their intended purpose.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed:

1. A needle assembly connectable to an injection device, the needle assembly comprising:
   a body;
   a luer-lock interface arranged on a rear side of the body;
   a needle for injecting or withdrawing fluids;
   the needle having a portion retained in the body and a piercing portion projecting forwardly from the portion retained in the body;
   a safety shield that is axially movable relative to the body at least between an initial position, an at least partially retracted position, and a post-use locking position; and
   a spring biasing the safety shield away from the at least partially retracted position,
   wherein the safety shield:
   locks in the post-use locking position via an internal locking system, wherein the internal locking system is prevented from being contacted by a user's fingers; and
   rotates at least partially as it moves from the initial position to the at least partially retracted position; and
   wherein the needle assembly has the following modes of operation when installed on an injection device:
   a first mode wherein the safety shield can move to a first retracted position during injection of the piercing portion of the needle into a container containing a substance that can be suctioned into the injection device;
   a second mode wherein the safety shield moves to a position protecting the piercing portion of the needle after the first mode;
   a third mode wherein the safety shield can move to a second retracted position during injection of the piercing portion of the needle into a surface that will receive the substance forced out of the injection device; and
   a fourth mode wherein the safety shield moves to a position protecting the piercing portion of the needle after the third mode.

2. The needle assembly of claim 1, wherein in the second mode the safety shield automatically moves to the position protecting the piercing portion of the needle after the first mode.

3. The needle assembly of claim 1, wherein in the fourth mode, the safety shield is locked in the position protecting the piercing portion of the needle so as to prevent re-use or re-injection of the needle.

4. The needle assembly of claim 1, wherein in the fourth mode the safety shield automatically moves to the position protecting the piercing portion of the needle after the third mode.

5. The needle assembly of claim 1, wherein in the fourth mode, the safety shield is locked in the position protecting the piercing portion of the needle so as to prevent re-use or re-injection of the needle.

6. The needle assembly of claim 1, wherein when in the fourth mode, the safety shield is prevented from moving back to a position exposing the piercing portion of the needle.

7. The needle assembly of claim 1, wherein the surface that will receive the substance forced out of the injection device is a skin surface.

8. The needle assembly of claim 1, wherein the needle assembly can be removably installed on the injection device.

9. A needle assembly connectable to an injection device, the needle assembly comprising:
- a body;
- a luer-lock interface arranged on a rear side of the body;
- a needle for injecting or withdrawing fluids;
- the needle having a portion retained in the body and a piercing portion projecting forwardly from the portion retained in the body;
- a safety shield that is axially movable relative to the body at least between an initial position, an at least partially retracted position, and a post-use locking position; and
- a spring biasing the safety shield away from the at least partially retracted position,
- wherein the safety shield:
- locks in the post-use locking position via an internal locking system, wherein the internal locking system is prevented from being contacted by a user's fingers; and
- rotates at least partially as it moves from the initial position to the at least partially retracted position; and
- wherein the needle assembly has the following modes of operation when installed on an injection device:
- a first mode wherein the safety shield can move to a first retracted position during injection of the piercing portion of the needle into a container containing a substance that can be suctioned into the injection device;
- a second mode wherein the safety shield moves to a position protecting the piercing portion of the needle after the first mode;
- a third mode wherein the safety shield moves to a position protecting the piercing portion of the needle after the second mode;
- a fourth mode wherein the safety shield can move to a second retracted position during injection of the piercing portion of the needle into a surface that will receive the substance forced out of the injection device; and
- a fifth mode wherein the safety shield moves to a position protecting the piercing portion of the needle after the fourth mode and is prevented from moving back to a position exposing the piercing portion of the needle.

10. The needle assembly of claim 9, wherein in the second mode the safety shield automatically moves to the position protecting the piercing portion of the needle after the first mode.

11. The needle assembly of claim 9, wherein in the fourth mode, the safety shield is locked in the position protecting the piercing portion of the needle so as to prevent re-use or re-injection of the needle.

12. The needle assembly of claim 9, wherein in the fourth mode the safety shield automatically moves to the position protecting the piercing portion of the needle after the third mode.

13. The needle assembly of claim 9, wherein in the fourth mode, the safety shield is locked in the position protecting the piercing portion of the needle so as to prevent re-use or re-injection of the needle.

14. The needle assembly of claim 9, wherein when in the fourth mode, the safety shield is prevented from moving back to a position exposing the piercing portion of the needle.

15. The needle assembly of claim 9, wherein the surface that will receive the substance forced out of the injection device is a skin surface.

16. The needle assembly of claim 9, wherein the needle assembly can be removably installed on the injection device.

* * * * *